United States Patent
Li et al.

(10) Patent No.: US 9,186,068 B2
(45) Date of Patent: Nov. 17, 2015

(54) METHODS AND SYSTEMS FOR PHOTOACOUSTIC MONITORING USING HYPERTONIC AND ISOTONIC INDICATOR DILUTIONS

(75) Inventors: Youzhi Li, Longmont, CO (US); Bo Chen, Louisville, CO (US); Lockett Wood, Lyons, CO (US); Ulf Borg, Longmont, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/310,859

(22) Filed: Dec. 5, 2011

(65) Prior Publication Data

US 2013/0144148 A1 Jun. 6, 2013

(51) Int. Cl.
*A61B 5/1455* (2006.01)
*A61B 5/00* (2006.01)
*A61B 5/029* (2006.01)

(52) U.S. Cl.
CPC ............ *A61B 5/0095* (2013.01); *A61B 5/029* (2013.01)

(58) Field of Classification Search
CPC .... A61B 5/0261; A61B 5/0275; A61B 5/029; A61B 5/0095
USPC .................................. 600/323, 338, 473, 476
See application file for complete search history.

(56) References Cited

U.S. PATENT DOCUMENTS

| | | | |
|---|---|---|---|
| 4,385,634 A | 5/1983 | Bowen | |
| 4,874,949 A * | 10/1989 | Harris et al. | 250/343 |
| 5,348,002 A | 9/1994 | Caro | |
| 5,657,754 A | 8/1997 | Rosencwaig | |
| 5,840,023 A | 11/1998 | Oraevsky et al. | |
| 5,941,821 A | 8/1999 | Chou | |
| 6,049,728 A | 4/2000 | Chou | |
| 6,104,942 A | 8/2000 | Kruger | |
| 6,309,352 B1 | 10/2001 | Oraevsky et al. | |
| 6,403,944 B1 | 6/2002 | MacKenzie et al. | |
| 6,405,069 B1 | 6/2002 | Oraevsky et al. | |
| 6,466,806 B1 | 10/2002 | Geva et al. | |
| 6,484,044 B1 | 11/2002 | Lilienfeld-Toal | |
| 6,498,942 B1 | 12/2002 | Esenaliev et al. | |
| 6,751,490 B2 | 6/2004 | Esenaliev et al. | |

(Continued)

FOREIGN PATENT DOCUMENTS

| | | |
|---|---|---|
| EP | 0282234 | 9/1988 |
| RU | 2238108 C1 | 10/2004 |
| WO | 9612440 A1 | 5/1996 |

OTHER PUBLICATIONS

Brecht, H., "Noninvasive Optoacoustic Monitoring of Blood Oxygenation in Large Blood Vessels," Thesis., The University of Texas Medical Branch, Dec. 2007.

(Continued)

*Primary Examiner* — Elmer Chao
(74) *Attorney, Agent, or Firm* — Fletcher Yoder PC

(57) ABSTRACT

A patient monitoring system may provide photoacoustic sensing based on an indicator dilution to determine one or more physiological parameters of a subject. The system may detect an acoustic pressure signal, which may include one or more thermo-dilution responses, one or more hemo-dilution responses, or a combination thereof. For example, a thermo-dilution indicator and/or a hemo-dilution indicator may be used to determine one or more hemodynamic parameters. In a further example, an isotonic indicator and a hypertonic indicator may be used to determine one or more hemodynamic parameters of the subject.

21 Claims, 8 Drawing Sheets

(56) References Cited

U.S. PATENT DOCUMENTS

| | | | |
|---|---|---|---|
| 6,839,496 | B1 | 1/2005 | Mills et al. |
| 6,846,288 | B2 | 1/2005 | Nagar et al. |
| 7,322,972 | B2 | 1/2008 | Viator et al. |
| 7,430,445 | B2 | 9/2008 | Esenaliev et al. |
| 7,515,948 | B1 | 4/2009 | Balberg et al. |
| 7,729,734 | B2 | 6/2010 | Mandelis et al. |
| 2006/0184042 | A1 | 8/2006 | Wang et al. |
| 2006/0189926 | A1* | 8/2006 | Hall et al. ............... 604/66 |
| 2006/0272418 | A1 | 12/2006 | Maris et al. |
| 2007/0197886 | A1 | 8/2007 | Naganuma et al. |
| 2008/0015434 | A1 | 1/2008 | Rubinstein et al. |
| 2008/0255433 | A1 | 10/2008 | Prough et al. |
| 2010/0152559 | A1 | 6/2010 | Cheng et al. |
| 2010/0285518 | A1 | 11/2010 | Viator et al. |
| 2010/0292547 | A1 | 11/2010 | Mandelis et al. |
| 2011/0201914 | A1 | 8/2011 | Wang et al. |
| 2011/0275890 | A1 | 11/2011 | Wang et al. |
| 2012/0029829 | A1 | 2/2012 | Li et al. |
| 2012/0197117 | A1* | 8/2012 | Picot et al. ............... 600/438 |

OTHER PUBLICATIONS

Esenaliev, R. O. et al., "Continuous, noninvasive monitoring of total hemoglobin concentration by an optoacoustic technique," Applied Optics, vol. 43, No. 17, pp. 3401-3407, 2007.

Guo, Z. et al., "Calibration-free absolute quantification of optical absorption coefficients using acoustic spectra in 3D photoacoustic microscopy of biological tissue," Optics Letters, vol. 35, No. 12, pp. 2067-2069, 2010.

Hu, S. et al., "Noninvasive label-free imaging of microhemodynamics by optical-respolution photoacustic microscopy," Optics Express, vol. 17, No. 9, pp. 7688-7694, 2009.

Petrova, I. Y. et al., "Clinical tests of highly portable, 2-lb, laser diode-based, noninvasive, optoacoustic hemoglobin monitor," Procedings of SPIE, vol. 7177, 717705, 2009.

Pramanik, M. et al., "Thermoacoustic and photoacoustic sensing of temperature," Journal of Biomedical Optics, vol. 14(5), 054024, 2009.

Ranasinghesagara, J. C. et al., "Combined photoacoustic and oblique-incidence diffuse reflectance system for quantitative photoacoustic imaging in turbid media," Journal of Biomedical Optics, vol. 15, 046016, 2010.

Guo, Z. et al., "On the speckle-free nature of photoacoustic tomography," Medical Physics, vol. 37, No. 9, pp. 4084-4088, 2009.

Fernandez-Mondejar, E. et al., "How important is the measurement of extravascular lung water?" Current Opinions in Critical Care, vol. 13, pp. 79-83, 2007.

Garland, J. S. et al., "Measurement of extravascular lung water in hemodialysis patients using blood ultrasound velocity and optical density dilution." ASAIO Journal, vol. 48, pp. 398-403.

Effros, R. M. et al., "Indicator dilution measurements of extravascular lung water: basic assumptions and observations," AJP—Lung Cellular and Molecular Physiology, vol. 294, pp. L1023-L1031, 2008.

Wintermark, M. et al., "Quantitative assessment of regional cerebral blood flows by perfusion CT studies at low injection rates." European Radiology, vol. 11, pp. 1220-1230, 2001.

Larina, I. V. et al. "Real-time optoacoustic montioring of temperature in tissues." Journal of Physics D: Applied Physics, vol. 38, pp. 2633-2639, 2005.

Isakow, W., et al. "Extravascular lung water measurements and hemodynamic monitoring in the critical ill." Am J. Physiol. Lung Cell Mol. Physiol. vol. 291, pp. L1118-L1131, 2006.

Krivitsky, N. M. et al., "vol. Of extravascular lung fluid determined by blood ultrasound velocity and electrical impedance dilution." ASAIO Journal, vol. 44, No. 5, pp. M535-M540, 1998.

Grodins, F. S., "Basic concepts in the determination of vascular volumes by indicator-dilution methods." Circulation Research, vol. 10, pp. 429-446, 1962.

Reuter, D. A. et al., "Cardiac output monitoring using indicator-dilution techniques: Basics, Limits, and Perspectives," Anesthesia and Analgesia, vol. 110, No. 3, pp. 799-811, 2010.

Telenkov, S. A. et al., "Photothermoacoustic imaging of biological tissues: maximum depth characterization comparison of time and frequency-domain measurements," Journal of Biomedical Optics, vol. 14(4), 044025, 2009.

International Preliminary Report on Patentability for PCT Application No. PCT/US2012/067770 dated Jun. 19, 2014; 5 pgs.

\* cited by examiner

METHODS AND SYSTEMS FOR PHOTOACOUSTIC MONITORING USING HYPERTONIC AND ISOTONIC INDICATOR DILUTIONS

The present disclosure relates to monitoring physiological parameters, and more particularly relates to monitoring physiological parameters using indicator dilution and photoacoustic analysis.

SUMMARY

A physiological monitoring system may be configured to determine a physiological parameter of a subject, using photoacoustic analysis and a dilution response. The system may include a light source that may provide a photonic signal to a first blood vessel site of the subject, which may be, for example, an artery of the subject. The system may also include an acoustic detector that detects an acoustic pressure signal from the first blood vessel site, caused by the absorption of at least some of the photonic signal by one or more constituents at the first blood vessel site.

In some embodiments, a hemo-dilution indicator, thermo-dilution indicator, or both, may be provided to a blood vessel site of the subject, which may be, for example, a vein of the subject. The one or more indicators may include a dye indicator, a saline indicator, or any other suitable type of indicator. A photoacoustic signal derived from the acoustic pressure signal may include one or more responses corresponding to one or more respective indicators. Based at least in part on the one or more responses, the system may determine one or more physiological parameters of the subject. The physiological parameters may include hemodynamic parameters such as, for example, cardiac output, intrathoracic blood volume, intrathoracic circulatory volume, global end-diastolic volume, pulmonary circulatory volume, extravascular lung water, and/or other suitable parameters. In some embodiments, one or more characteristics may be derived from an acoustic pressure signal such as, for example, a value of the acoustic pressure signal, a value of a signal derived from the acoustic pressure signal such as a photoacoustic signal, an area under a dilution curve derived from the photoacoustic signal, a time, or a time difference, and may be used to determine the one or more physiological parameters.

In some embodiments, an isotonic indicator and a hypertonic indicator may be provided to the subject at a second blood vessel site, which may be, for example, a central vein. The photoacoustic signal may include a first response corresponding to the isotonic indicator and a second response corresponding to the hypertonic indicator. Based at least in part on the first and second response, the system may determine one or more physiological parameters of the subject. The physiological parameters may include hemodynamic parameters such as, for example, cardiac output and extravascular lung water. In some embodiments, at least one of the isotonic indicator and the hypertonic indicator comprises a dye indicator. In some embodiments, the system may generate a dilution curve, and determine the one or more physiological parameters based at least in part on the dilution curve.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
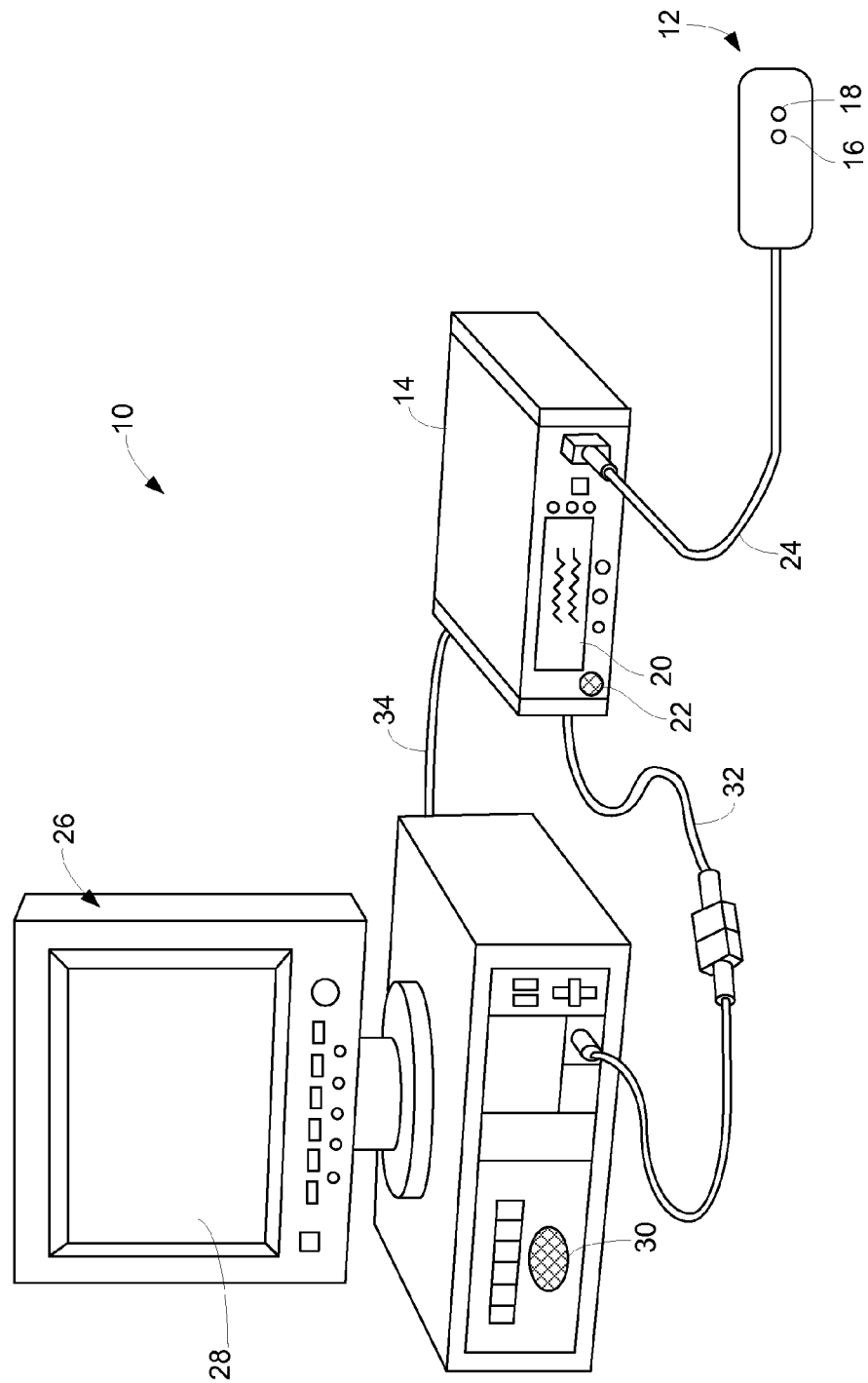
FIG. 1 shows an illustrative physiological monitoring system, in accordance with some embodiments of the present disclosure.

Photoacoustics (or "optoacoustics") or the photoacoustic effect (or "optoacoustic effect") refers to the phenomenon in which one or more wavelengths of light are presented to and absorbed by one or more constituents of an object, thereby causing an increase in kinetic energy of the one or more constituents, which causes an associated pressure response within the object. Particular modulations or pulsing of the incident light, along with measurements of the corresponding pressure response in, for example, tissue of the subject, may be used for medical imaging, physiological parameter determination, or both. For example, the concentration of a constituent, such as hemoglobin (e.g., oxygenated, deoxygenated and/or total hemoglobin) may be determined using photoacoustic analysis. In a further example, one or more hemodynamic parameters such as cardiac output, intrathoracic blood volume, intrathoracic circulatory volume, global end-diastolic volume, pulmonary circulatory volume, extravascular lung water, and/or any other suitable hemodynamic parameters may be determined using photoacoustic analysis and indicator dilution techniques.

A photoacoustic system may include a photoacoustic sensor that is placed at a site on a subject, typically the wrist, palm, neck, forehead, temple, or anywhere an artery or vessel is accessible noninvasively. In some embodiments, the photoacoustic techniques described herein are used to monitor large blood vessels, such as a major artery or vein which may be near the heart (e.g., the carotid or radial arteries or the jugular vein). The photoacoustic system may use a light source, and any suitable light guides (e.g., fiber optics), to pass light through the subject's tissue, or a combination of tissue thereof (e.g., organs), and an acoustic detector to sense the pressure response of the tissue induced by the light absorption by a blood vessel. Tissue may include muscle, fat, blood, blood vessels, and/or any other suitable tissue types. In some embodiments, the light source may be a laser or laser diode, operated in pulsed or continuous wave (CW) mode. In some embodiments, the acoustic detector may be an ultrasound detector, which may be suitable to detect pressure fluctuations arising from the constituent's absorption of the incident light of the light source.

In some embodiments, the light from the light source may be focused, shaped, or otherwise spatially modulated to illuminate a particular region of interest. In some arrangements, photoacoustic monitoring may allow relatively higher spatial resolution than line of sight optical techniques (e.g., path integrated absorption measurements). The enhanced spatial resolution of the photoacoustic technique may allow for imaging, scalar field mapping, and other spatially resolved results, in 1, 2, or 3 spatial dimensions. The acoustic response to the photonic excitation may radiate from the illuminated region of interest, and accordingly may be detected at multiple positions.

The photoacoustic system may measure the pressure response that is received at the acoustic sensor as a function of time. The photoacoustic system may also include sensors at multiple locations. A signal representing pressure versus time or a mathematical manipulation of this signal (e.g., a scaled version thereof, etc.) may be referred to as the photoacoustic (PA) signal. The PA signal may be derived from a detected acoustic pressure signal by selecting a suitable subset of points of an acoustic pressure signal. The PA signal may be used to calculate any of a number of physiological parameters, including a concentration of a blood constituent (e.g., hemoglobin), at a particular spatial location. In some embodiments, PA signals from multiple spatial locations may be used to construct an image (e.g., imaging blood vessels) or a scalar field (e.g., a hemoglobin concentration field). In some embodiments, an indicator such as, for example, a dye or saline solution may be introduced into the blood stream of a subject, and the PA system may be used to determine a concentration of a blood constituent, a concentration of an indicator, a relative temperature difference, any suitable characteristic of an indicator dilution response, any suitable hemodynamic parameters derived thereof, any other suitable parameter, or any combination thereof.

In some applications, the light passed through the tissue is selected to be of one or more wavelengths that are absorbed by the constituent in an amount representative of the amount of the constituent present in the tissue. The absorption of light passed through the tissue varies in accordance with the amount of the constituent in the tissue. For example, Red and/or infrared (IR) wavelengths may be used because highly oxygenated blood will absorb relatively less Red light and more IR light than blood with a lower oxygen saturation.

Any suitable light source may be used, and characteristics of the light provided by the light source may be controlled in any suitable manner. In some embodiments, a pulsed light source may be used to provide relatively short-duration pulses (e.g., nanosecond pulses) of light to the region of interest. Accordingly, the use of a pulse light source may result in a relatively broadband acoustic response (e.g., depending on the pulse duration). The use of a pulsed light source will be referred to herein as the "Time Domain Photoacoustic" (TD-PA) technique. A convenient starting point for analyzing a TD-PA signal is given by Eq. 1:

$$p(z) = \Gamma \mu_a \phi(z) \tag{1}$$

under conditions where the irradiation time is small compared to the characteristic thermal diffusion time determined by the properties of the specific tissue type. Referring to Eq. 1, $p(z)$ is the PA signal (indicative of the maximum induced pressure rise, derived from an acoustic pressure signal) at spatial location z indicative of acoustic pressure, $\Gamma$ is the dimensionless Grüneisen parameter of the tissue, $\mu_a$ is the effective absorption coefficient of the tissue (or constituent thereof) to the incident light, and $\phi(z)$ is the optical fluence at spatial location z. The Grüneisen parameter is a dimensionless description of thermoelastic effects, and may be illustratively formulated by Eq. 2:

$$\Gamma = \frac{\beta c_a^2}{C_P} \tag{2}$$

where $c_a$ is the speed of sound in the tissue, $\beta$ is the isobaric volume thermal expansion coefficient, and $C_P$ is the specific heat at constant pressure. In some circumstances, the optical fluence, at spatial location z (within the subject's tissue) of interest may be dependent upon the light source, the location itself (e.g., the depth), and optical properties (e.g., scattering coefficient, absorption coefficient, or other properties) along the optical path. For example, Eq. 3 provides an illustrative expression for the attenuated optical fluence at a depth z:

$$\phi(z) = \phi_0 e^{-\mu_{eff} z} \tag{3}$$

where $\phi_0$ is the optical fluence from the light source incident at the tissue surface, z is the path length (i.e., the depth into the tissue in this example), and $\mu_{eff}$ is an effective attenuation coefficient of the tissue along the path length in the tissue in this example.

In some embodiments, a more detailed expression or model may be used rather than the illustrative expression of Eq. 3. In some embodiments, the actual pressure encountered by an acoustic detector may be proportional to Eq. 1, as the focal distance and solid angle (e.g., face area) of the detector may affect the actual measured PA signal. In some embodiments, an ultrasound detector positioned relatively farther away from the region of interest, will encounter a relatively smaller acoustic pressure. For example, the peak acoustic pressure signal received at a circular area $A_d$ positioned at a distance R from the illuminated region of interest may be given by Eq. 4:

$$p_d = p(z) f(r_s, R, A_d) \tag{4}$$

where $r_s$ is the radius of the illuminated region of interest (and typically $r_s < R$), and $p(z)$ is given by Eq. 1. In some embodiments, the detected acoustic pressure amplitude may decrease as the distance R increases (e.g., for a spherical acoustic wave).

In some embodiments, a modulated CW light source may be used to provide a photonic excitation of a tissue constituent to cause a photoacoustic response in the tissue. The CW light source may be intensity modulated at one or more characteristic frequencies. The use of a CW light source, intensity modulated at one or more frequencies, will be referred to herein as the "Frequency Domain Photoacoustic" (FD-PA) technique. Although the FD-PA technique may include using frequency domain analysis, the technique may use time domain analysis, wavelet domain analysis, or any other suitable analysis, or any combination thereof. Accordingly, the term "frequency domain" as used in "FD-PA" refers to the frequency modulation of the photonic signal, and not to the type of analysis used to process the photoacoustic response.

Under some conditions, the acoustic pressure p(R,t) at detector position R at time t, may be shown illustratively by Eq. 5:

$$p(R, t) \sim \frac{p_0(r_0, \omega)}{R} e^{-i\omega(t-\tau)} \quad (5)$$

where $r_0$ is the position of the illuminated region of interest, $\omega$ is the angular frequency of the acoustic wave (caused by modulation of the photonic signal at frequency $\omega$), R is the distance between the illuminated region of interest and the detector, and $\tau$ is the travel time delay of the wave equal to $R/c_a$, where $c_a$ is the speed of sound in the tissue. The FD-PA spectrum $p_0(r_0,\omega)$ of acoustic waves is shown illustratively by Eq. 6:

$$p_0(r_0, \omega) = \frac{\Gamma \mu_a \phi(r_0)}{2(\mu_a c_a - i\omega)} \quad (6)$$

where $\mu_a r_a$ represents a characteristic frequency (and corresponding time scale) of the tissue.

In some embodiments, a FD-PA system may temporally vary the characteristic modulation frequency of the CW light source, and accordingly the characteristic frequency of the associated acoustic response. For example, the FD-PA system may use linear frequency modulation (LFM), either increasing or decreasing with time, which is sometimes referred to as "chirp" signal modulation. Shown in Eq. 7 is an illustrative expression for a sinusoidal chirp signal r(t):

$$r(t) = \sin\left(t\left(\omega_0 + \frac{b}{2}t\right)\right) \quad (7)$$

where $\omega_0$ is a starting angular frequency, and b is the angular frequency scan rate. Any suitable range of frequencies (and corresponding angular frequencies) may be used for modulation such as, for example, 1-5 MHz, 200-800 kHz, or other suitable range, in accordance with the present disclosure. In some embodiments, signals having a characteristic frequency that changes as a nonlinear function of time may be used. Any suitable technique, or combination of techniques thereof, may be used to analyze a FD acoustic pressure signal. Two such exemplary techniques, a correlation technique and a heterodyne mixing technique, will be discussed below as illustrative examples.

In some embodiments, the correlation technique may be used to determine the travel time delay of the FD-PA signal. In some embodiments, a matched filtering technique may be used to process a PA signal. As shown in Eq. 8:

$$B_S(t-\tau) = \frac{1}{2\pi} \int_{-\infty}^{\infty} H(\omega)S(\omega)e^{i\omega t} d\omega \quad (8)$$

Fourier transforms (and inverse transforms) are used to calculate the filter output $B_s(t-T)$, in which $H(\omega)$ is the filter frequency response, $S(\omega)$ is the Fourier transform of the PA signal s(t), and T is the phase difference between the filter and signal. In some circumstances, the filter output of expression of Eq. 8 may be equivalent to an autocorrelation function. Shown in Eq. 9:

$$S(\omega) = \frac{1}{2\pi} \int_{-\infty}^{\infty} s(t)e^{-i\omega t} dt \quad (9)$$

is an expression for computing the Fourier transform $S(\omega)$ of the PA signal s(t). Shown in Eq. 10:

$$H(\omega) = S^*(\omega)e^{-i\omega \tau} \quad (10)$$

is an expression for computing the filter frequency response $H(\omega)$ based on the Fourier transform of the PA signal s(t), in which $S^*(\omega)$ is the complex conjugate of $S(\omega)$. It can be observed that the filter frequency response of Eq. 10 requires the frequency character of the PA signal be known beforehand to determine the frequency response of the filter. In some embodiments, as shown by Eq. 11:

$$B(t) = \int_{-\infty}^{\infty} r(t')s(t+t') dt' \quad (11)$$

the known modulation signal r(t) may be used for generating a cross-correlation with the PA signal. The cross-correlation output B(t) of Eq. 11 is expected to exhibit a peak at a time t equal to the acoustic signal travel time $\tau$. Assuming that the temperature response and resulting acoustic response follow the illumination modulation (e.g., are coherent), Eq. 11 may allow calculation of the time delay, depth information, or both.

In some embodiments, the heterodyne mixing technique may be used to determine the travel time delay of the FD-PA signal. The FD-PA signal, as described above, may have similar frequency character as the modulation signal (e.g., coherence), albeit shifted in time due to the travel time of the acoustic signal. For example, a chirp modulation signal, such as r(t) of Eq. 7, may be used to modulate a CW light source. Heterodyne mixing uses the trigonometric identity of the following Eq. 12:

$$\sin(A)\sin(B) = \frac{1}{2}[\cos(A-B) - \cos(A+B)] \quad (12)$$

which shows that two signals may be combined by multiplication to give periodic signals at two distinct frequencies (i.e., the sum and the difference of the original frequencies). If the result is passed through a low-pass filter to remove the higher frequency term (i.e., the sum), the resulting filtered, frequency shifted signal may be analyzed. For example, Eq. 13 shows a heterodyne signal L(t):

$$L(t) = \langle r(t)s(t) \rangle \cong \left\langle Kr(t)r\left(t - \frac{R}{c_a}\right)\right\rangle = \frac{1}{2}K\cos\left(\frac{R}{c_a}bt + \theta\right) \quad (13)$$

calculated by low-pass filtering (shown by angle brackets) the product of modulation signal r(t) and PA signal s(t). If the PA signal is assumed to be equivalent to the modulation signal, with a time lag $R/c_a$ due to travel time of the acoustic wave and amplitude scaling K, then a convenient approximation of Eq. 13 may be made, giving the rightmost expression of Eq. 13. Analysis of the rightmost expression of Eq. 13 may provide depth information, travel time, or both. For example, a fast Fourier transform (FFT) may be performed on the heterodyne signal, and the frequency associated with the highest peak may be considered equivalent to time lag $Rb/c_a$. Assuming that the frequency scan rate b and the speed of sound $c_a$ are known, the depth R may be estimated.

In some embodiments, a photoacoustic signal may be used with Eq. 1 to determine an absorption coefficient $\mu_a$. When a suitable light source is used (e.g., a photonic signal at 905 nm), tHb may be determined based on the value of the absorption coefficient and one or more pre-defined parameters. In some embodiments, a photonic signal may include light have two different wavelengths (e.g., one of which may be 905 nm), and blood oxygen saturation may be determined based on photoacoustic signals corresponding to the each wavelength of the photonic signal. In some embodiments, a light source may provide a photonic signal including light having a wavelength at an isobestic point where light absorption of oxy and de-oxy hemoglobin are substantially equal (e.g., at about 808 nm).

FIG. 1 is a perspective view of an embodiment of a physiological monitoring system 10. System 10 may include sensor unit 12 and monitor 14. In some embodiments, sensor unit 12 may be part of a photoacoustic monitor or imaging system. Sensor unit 12 may include a light source 16 for emitting light at one or more wavelengths, which may but need not correspond to visible light, into a subject's tissue. Light source 16 may provide a photonic signal including any suitable electromagnetic radiation such as, for example, a radio wave, a microwave wave, an infrared wave, a visible light wave, ultraviolet wave, any other suitable light wave, or any combination thereof. A detector 18 may also be provided in sensor unit 12 for detecting the acoustic (e.g., ultrasound) response that travels through the subject's tissue. Any suitable physical configuration of light source 16 and detector 18 may be used. In an embodiment, sensor unit 12 may include multiple light sources and/or acoustic detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12 (e.g., a photoplethysmograph sensor). Multiple sensor units may be capable of being positioned at two different locations on a subject's body.

In some embodiments, system 10 may include two or more sensors forming a sensor array in lieu of either or both of the sensor units. In some embodiments, a sensor array may include multiple light sources, detectors, or both. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data relating to light emission and acoustic detection received from one or more sensor units such as sensor unit 12. For example, monitor 14 may be configured to determine cardiac output, intrathoracic blood volume, intrathoracic circulatory volume, global end-diastolic volume, pulmonary circulatory volume, extravascular lung water, any other suitable hemodynamic parameters, or any combination thereof. Further, monitor 14 may be configured to determine pulse rate, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a subject's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. Cable 24 may include electronic conductors (e.g., wires for transmitting electronic signals from detector 18), optical fibers (e.g., multi-mode or single-mode fibers for transmitting emitted light from light source 16), any other suitable components, any suitable insulation or sheathing, or any combination thereof. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may be allow communication between monitor 14 and sensor unit 12.

In the illustrated embodiment, system 10 includes a multiparameter physiological monitor 26. The monitor 26 may include a cathode ray tube display, a flat panel display (as shown) such as a liquid crystal display (LCD) or a plasma display, or may include any other type of monitor now known or later developed. Multi-parameter physiological monitor 26 may be configured to calculate physiological parameters and to provide a display 28 for information from monitor 14 and from other medical monitoring devices or systems (not shown). For example, multi-parameter physiological monitor 26 may be configured to display an estimate of a subject's extravascular lung water, cardiac output, and hemoglobin concentration generated by monitor 14. Multi-parameter physiological monitor 26 may include a speaker 30.

Monitor 14 may be communicatively coupled to multi-parameter physiological monitor 26 via a cable 32 or 34 that is coupled to a sensor input port or a digital communications port, respectively and/or may communicate wirelessly (not shown). In addition, monitor 14 and/or multi-parameter physiological monitor 26 may be coupled to a network to enable the sharing of information with servers or other workstations (not shown). Monitor 14 may be powered by a battery (not shown) or by a conventional power source such as a wall outlet.

Figure 2:
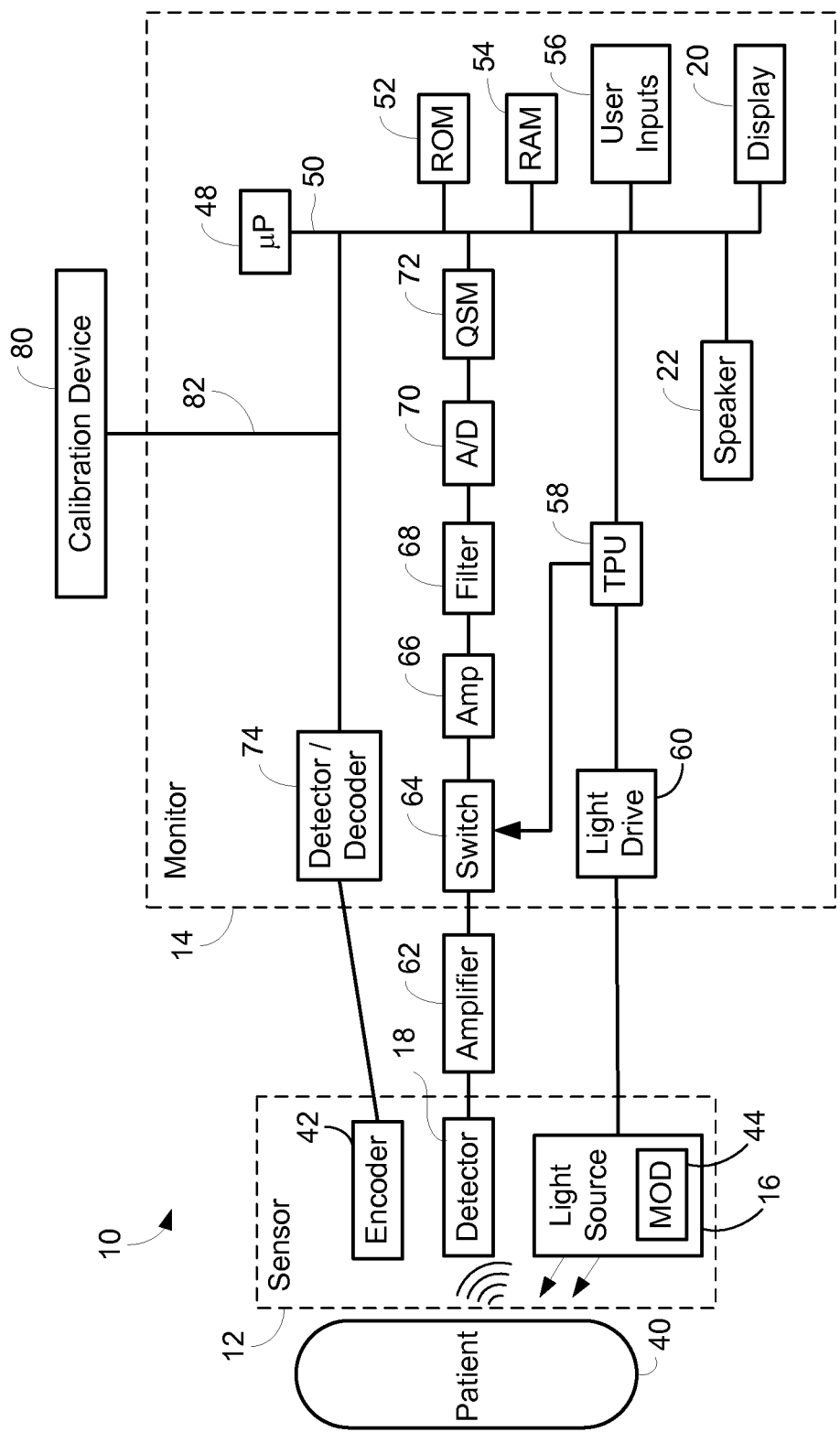
FIG. 2 is a block diagram of the illustrative physiological monitoring system of FIG. 1 coupled to a subject, in accordance with some embodiments of the present disclosure.

FIG. 2 is a block diagram of a physiological monitoring system, such as physiological monitoring system 10 of FIG. 1, which may be coupled to a subject 40 in accordance with an embodiment. Certain illustrative components of sensor unit 12 and monitor 14 are illustrated in FIG. 2.

Sensor unit 12 may include light source 16, detector 18, and encoder 42. In some embodiments, light source 16 may be configured to emit one or more wavelengths of light (e.g., visible, infrared) into a subject's tissue 40. Hence, light source 16 may provide Red light, IR light, any other suitable light, or any combination thereof, that may be used to calculate the subject's physiological parameters. In some embodiments, a Red wavelength may be between about 600 nm and about 700 nm. In some embodiments, an IR wavelength may be between about 800 nm and about 1000 nm. In embodiments where a sensor array is used in place of a single sensor, each sensor may be configured to provide light of a single wavelength. For example, a first sensor may emit only a Red light while a second may emit only an IR light. In a further example, the wavelengths of light used may be selected based on the specific location of the sensor. In a further example, one or more sensors may provide light at about 730 nm, about 810 nm, and/or about 900 nm.

It will be understood that, as used herein, the term "light" may refer to energy produced by electromagnetic radiation sources. Light may be of any suitable wavelength and intensity, and modulations thereof, in any suitable shape and direction. Detector 18 may be chosen to be specifically sensitive to the acoustic response of the subject's tissue arising from use of light source 16. It will also be understood that, as used herein, the "acoustic response" shall refer to pressure and changes thereof caused by a thermal response (e.g., expansion and contraction) of tissue to light absorption by the tissue or constituent thereof.

In some embodiments, detector 18 may be configured to detect the acoustic response of tissue to the photonic excitation caused by the light source. In some embodiments, detector 18 may be a piezoelectric transducer which may detect force and pressure and output an electrical signal via the piezoelectric effect. In some embodiments, detector 18 may be a Faby-Pérot interferometer, or etalon. For example, a thin film (e.g., composed of a polymer) may be irradiated with reference light, which may be internally reflected by the film. Pressure fluctuations may modulate the film thickness, thus causing changes in the reference light reflection which may be measured and correlated with the acoustic pressure. In some embodiments, detector 18 may be configured or otherwise tuned to detect acoustic response in a particular frequency range. Detector 18 may convert the acoustic pressure signal into an electrical signal (e.g., using a piezoelectric material, photodetector of a Faby-Pérot interferometer, or other suitable device). After converting the received acoustic pressure signal to an electrical, optical, and/or wireless signal, detector 18 may send the signal to monitor 14, where physiological parameters may be calculated based on the photoacoustic activity within the subject's tissue 40. The signal outputted from detector 18 and/or a pre-processed signal derived thereof, will be referred to herein as a photoacoustic signal.

In some embodiments, encoder 42 may contain information about sensor unit 12, such as what type of sensor it is (e.g., where the sensor is intended to be placed on a subject), the wavelength(s) of light emitted by light source 16, the intensity of light emitted by light source 16 (e.g., output wattage or Joules), the mode of light source 16 (e.g., pulsed versus CW), any other suitable information, or any combination thereof. This information may be used by monitor 14 to select appropriate algorithms, lookup tables and/or calibration coefficients stored in monitor 14 for calculating the subject's physiological parameters.

Encoder 42 may contain information specific to subject 40, such as, for example, the subject's age, weight, and diagnosis. This information about a subject's characteristics may allow monitor 14 to determine, for example, subject-specific threshold ranges in which the subject's physiological parameter measurements should fall and to enable or disable additional physiological parameter algorithms. Encoder 42 may, for instance, be a coded resistor that stores values corresponding to the type of sensor unit 12 or the type of each sensor in the sensor array, the wavelengths of light emitted by light source 16 on each sensor of the sensor array, and/or the subject's characteristics. In some embodiments, encoder 42 may include a memory on which one or more of the following information may be stored for communication to monitor 14: the type of the sensor unit 12; the wavelengths of light emitted by light source 16; the particular acoustic range that each sensor in the sensor array is monitoring; the particular acoustic spectral characteristics of a detector; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control the activation of light source 16. For example, TPU 58 may control pulse timing (e.g., pulse duration and inter-pulse interval) for TD-PA monitoring system. TPU 58 may also control the gating-in of signals from detector 18 through amplifier 62 and switching circuit 64. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In the embodiment shown, light source 16 may include modulator 44, in order to, for example, perform FD-PA analysis. Modulator 44 may be configured to provide intensity modulation, spatial modulation, any other suitable optical signal modulations, or any combination thereof. For example, light source 16 may be a CW light source, and modulator 44 may provide intensity modulation of the CW light source such as using a linear sweep modulation. In some embodiments, modulator 44 may be included in light drive 60, or other suitable components of physiological monitoring system 10, or any combination thereof.

In some embodiments, microprocessor 48 may determine the subject's physiological parameters, such as $SpO_2$, $SvO_2$, oxy-hemoglobin concentration, deoxy-hemoglobin concentration, total hemoglobin concentration (tHb), pulse rate, cardiac output, intrathoracic blood volume, intrathoracic circulatory volume, global end-diastolic volume, pulmonary circulatory volume, extravascular lung water, and/or other physiological parameters, using various algorithms and/or lookup tables based on the value of the received signals and/or data corresponding to the acoustic response received by detector 18. Signals corresponding to information about subject 40, and particularly about the acoustic signals emanating from a subject's tissue over time, may be transmitted from encoder 42 to decoder 74. These signals may include, for example, encoded information relating to subject characteristics. Decoder 74 may translate these signals to enable the microprocessor to determine the thresholds based at least in part on algorithms or lookup tables stored in ROM 52. In some embodiments, user inputs 56 may be used to enter information, select one or more options, provide a response, input settings, provide any other suitable inputting function, or any combination thereof. User inputs 56 may be used to enter information about the subject such as, for example, age, weight, height, diagnosis, medications, treatments, and so forth. In some embodiments, display 20 may exhibit a list of values, which may generally apply to the subject, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

The acoustic signal attenuated by the tissue of subject 40 can be degraded by noise, among other sources. Movement of the subject may also introduce noise and affect the signal. For example, the contact between the detector and the skin, or the light source and the skin, can be temporarily disrupted when movement causes either to move away from the skin. Another potential source of noise is electromagnetic coupling from other electronic instruments.

Noise (e.g., from subject movement) can degrade a sensor signal relied upon by a care provider, without the care provider's awareness. This is especially true if the monitoring of the subject is remote, the motion is too small to be observed, or the care provider is watching the instrument or other parts of the subject, and not the sensor site. Processing sensor signals may involve operations that reduce the amount of noise present in the signals, control the amount of noise present in the signal, or otherwise identify noise components in order to prevent them from affecting measurements of physiological parameters derived from the sensor signals.

Figure 3:
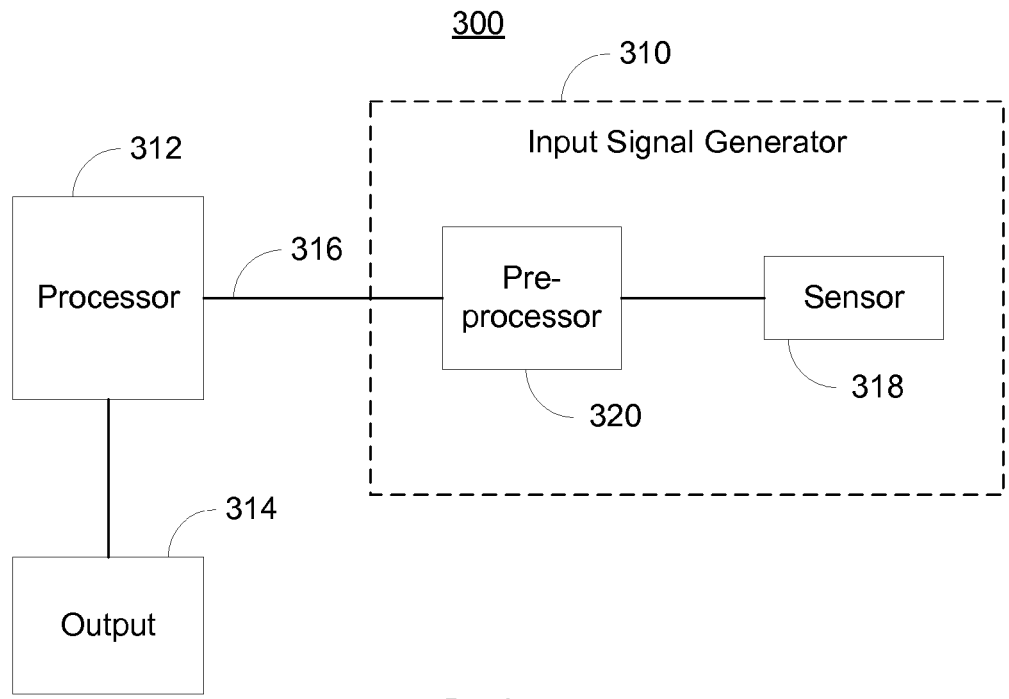
FIG. 3 is a block diagram of an illustrative signal processing system, in accordance with some embodiments of the present disclosure.

FIG. 3 is an illustrative signal processing system 300 in accordance with an embodiment that may implement the signal processing techniques described herein. In some embodiments, signal processing system 300 may be included in a physiological monitoring system (e.g., physiological monitoring system 10 of FIGS. 1-2). In the illustrated embodiment, input signal generator 310 generates an input signal 316. As illustrated, input signal generator 310 may include pre-processor 320 coupled to sensor 318, which may provide input signal 316. In some embodiments, pre-processor 320 may be a photoacoustic module and input signal 316 may be a photoacoustic signal. In an embodiment, pre-processor 320 may be any suitable signal processing device and input signal 316 may include one or more photoacoustic signals and one or more other physiological signals, such as a photoplethysmograph signal. It will be understood that input signal generator 310 may include any suitable signal source, signal generating data, signal generating equipment, or any combination thereof to produce input signal 316. Input signal 316 may be a single signal, or may be multiple signals transmitted over a single pathway or multiple pathways.

Pre-processor 320 may apply one or more signal processing operations to the signal generated by sensor 318. For example, pre-processor 320 may apply a predetermined set of processing operations to the signal provided by sensor 318 to produce input signal 316 that can be appropriately interpreted by processor 312, such as performing A/D conversion. In some embodiments, A/D conversion may be performed by processor 312. Pre-processor 320 may also perform any of the following operations on the signal provided by sensor 318: reshaping the signal for transmission, multiplexing the signal, modulating the signal onto carrier signals, compressing the signal, encoding the signal, and filtering the signal.

In some embodiments, input signal 316 may be coupled to processor 312. Processor 312 may be any suitable software, firmware, hardware, or combination thereof for processing input signal 316. For example, processor 312 may include one or more hardware processors (e.g., integrated circuits), one or more software modules, and computer-readable media such as memory, firmware, or any combination thereof. Processor 312 may, for example, be a computer or may be one or more chips (i.e., integrated circuits) such as, for example, a field programmable gate array (FPGA), micro-controller, or digital signal processor (DSP). Processor 312 may, for example, include an assembly of analog electronic components. Processor 312 may calculate physiological information. For example, processor 312 may perform time domain calculations, spectral domain calculations, time-spectral transformations (e.g., fast Fourier transforms, inverse fast Fourier transforms), any other suitable calculations, or any combination thereof. Processor 312 may perform any suitable signal processing of input signal 316 to filter input signal 316, such as any suitable band-pass filtering, adaptive filtering, closed-loop filtering, any other suitable filtering, and/or any combination thereof. Processor 312 may also receive input signals from additional sources (not shown). For example, processor 312 may receive an input signal containing information about treatments provided to the subject. Additional input signals may be used by processor 312 in any of the calculations or operations it performs in accordance with processing system 300.

In some embodiments, all or some of pre-processor 320, processor 312, or both, may be referred to collectively as processing equipment. For example, processing equipment may be configured to amplify, filter, sample and digitize input signal 316 (e.g., using an analog to digital converter), and calculate physiological information from the digitized signal.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. In some embodiments, processor 312 may store physiological measurements or previously received data from signal 316 in a memory device for later retrieval. In some embodiments, processor 312 may store calculated values, such as pulse rate, blood pressure, blood oxygen saturation (e.g., arterial, venous, or both), hemoglobin concentration (e.g., oxygenated, deoxygenated, and/or total), cardiac output, intrathoracic blood volume, intrathoracic circulatory volume, global end-diastolic volume, pulmonary circulatory volume, extravascular lung water, or any other suitable calculated values, or combinations thereof, in a memory device for later retrieval.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as part of sensor unit 12 (FIGS. 1 and 2) and monitor 14 (FIGS. 1 and 2) and processor 312 may be implemented as part of monitor 14 (FIGS. 1 and 2). In some embodiments, portions of system 300 may be configured to be portable. For example, all or part of system 300 may be embedded in a small, compact object carried with or attached to the subject (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous physiological monitoring solution. In some embodiments, a wireless transceiver (not shown) may also be included in system 300 to enable wireless communication with other components of system 10. For example, pre-processor 320 may output signal 316 (e.g., which may be a pre-processed photoacoustic signal) over BLUETOOTH, IEEE 802.11, WiFi, WiMax, cable, satellite, Infrared, any other suitable transmission scheme, or any combination thereof. In some embodiments, a wireless transmission scheme may be used between any communicating components of system 300.

It will also be understood that while some of the equations referenced herein are continuous functions, the processing equipment may be configured to use digital or discrete forms of the equation in processing the acquired PA signal.

Figure 4:
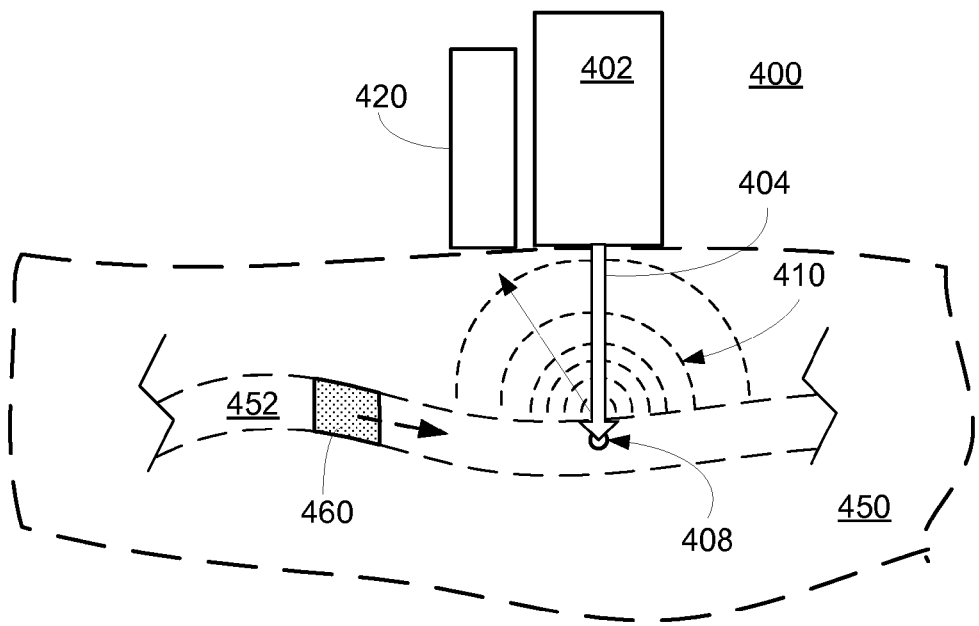
FIG. 4 shows an illustrative photoacoustic arrangement, in accordance with some embodiments of the present disclosure.

FIG. 4 shows an illustrative photoacoustic arrangement 400, in accordance with some embodiments of the present disclosure. Light source 402, controlled by a suitable light drive (e.g., a light drive of system 300 or system 10, although not shown in FIG. 4), may provide photonic signal 404 to subject 450. Photonic signal 404 may be attenuated along its pathlength in subject 450 prior to reaching site 408 of blood vessel 452, and may be attenuated across blood vessel 452. It will be understood that photonic signal 404 may scatter in subject 450 and need not travel as a constant, well-formed beam as illustrated. Also, photonic signal 404 may generally travel through and beyond site 408, although not illustrated in FIG. 4. A constituent of the blood in blood vessel 452 such as, for example, hemoglobin, or an injected indicator (e.g., a dye) may absorb at least some of photonic signal 404 at site 408. Accordingly, the blood may exhibit an acoustic pressure response via the photoacoustic effect, which may act on the surrounding tissues of blood vessel 452. Acoustic detector 420 may detect acoustic pressure signals 410 traveling though tissue of subject 450, and output (not shown) a photoacoustic signal that may be processed by suitable processing equipment. Changes in some properties of the blood in blood vessel 452 at site 408 may be detected by acoustic detector 420. For example, a reduced hemoglobin concentration or reduced temperature at the monitoring site may cause a reduced acoustic pressure signal to be detected by acoustic detector 420. In some embodiments, bolus dose 460, which may include a suitable indicator, may be introduced to the blood of patient 450 at a suitable blood vessel site (not shown in FIG. 4). Acoustic detector 420 may detect the transient changes in the hemoglobin concentration ("hemo-dilution") and/or temperature ("thermo-dilution") at site 408 due to passage of bolus dose 460 through site 408. In some embodiments (not shown), multiple monitoring sites may be used to detect changes in hemoglobin concentration, temperature, or both. As bolus dose 460 travels through the circulatory system of subject 450, diffusion, mixing (e.g., within a heart chamber), or both may spread the hemoglobin concentration and temperature profiles axially (i.e., in the direction of flow) and radially (i.e., normal to the direction of flow). It will be understood that hemo-dilution refers to the dilution of blood constituents caused by the bolus dose, and thermo-dilution refers to the combined effects of blood constituent dilution and temperature change, both caused by the bolus dose. In some embodiments, by using a thermo-dilution indicator, a temperature change may be enhanced by hemo-dilution (e.g., when the temperature change and the dilution change both cause the photoacoustic signal to either increase or decrease), and accordingly may be detected by a system having relatively less temperature sensitivity.

Dilution techniques using a bolus dose may be used to determine, for example, cardiac output (CO), intrathoracic blood volume (ITBV), intrathoracic circulatory volume (ITCV), global end-diastolic volume (GEDV), pulmonary circulatory volume (PCV), extravascular lung water (EVLW), and/or other hemodynamic parameters.

A bolus dose of an indicator may cause the properties at a photoacoustic monitoring site to change in time as the bolus dose passes the site. Introduction of the indicator may alter one or more properties of the blood that interacts with the indicator (e.g., blood near the bolus dose). An indicator introduced as a bolus dose may be selected to have one or more properties that allow the bolus dose to be distinguished from a subject's un-dosed blood. For example, an indicator may be selected which has particular absorption properties at one or more particular wavelengths (e.g., a dye indicator such as indocyanine green dye), and the photoacoustic monitoring system may monitor the presence of the indicator by providing a photonic signal at the one or more particular wavelengths and detecting an acoustic pressure signal having a dye indicator dilution response. In a further example, an indicator may be selected to dilute blood of a subject but not substantially absorb the photonic signal. The photoacoustic monitoring system may then accordingly monitor the blood (e.g., hemoglobin) rather than the indicator, to detect dilution. In a further example, an indicator having a temperature different from the temperature of the subject's un-dosed blood may be introduced into a subject's bloodstream (e.g., a "hot" or "cold" indicator, relative to the blood temperature). The photoacoustic monitoring system may then accordingly monitor the bloodstream temperature at the monitoring site, or the combined effects of hemo-dilution and thermo-dilution achieved by the bolus dose. In some embodiments, an indicator may have more than one property that may be distinguished from a subject's blood. For example, a cold dye indicator may be introduced to the subject's bloodstream, which may allow hemo-dilution and thermo-dilution effects to be detected. In some embodiments, more than one indicator may be introduced to the subject's bloodstream, each indicator having particular properties that may be unique relative to the other indicators. For example, an isotonic indicator and a hypertonic indicator may be introduced into a subject's bloodstream. In a further example, a cold isotonic indicator and a dye indicator may be introduced into a subject's bloodstream.

Figure 5:
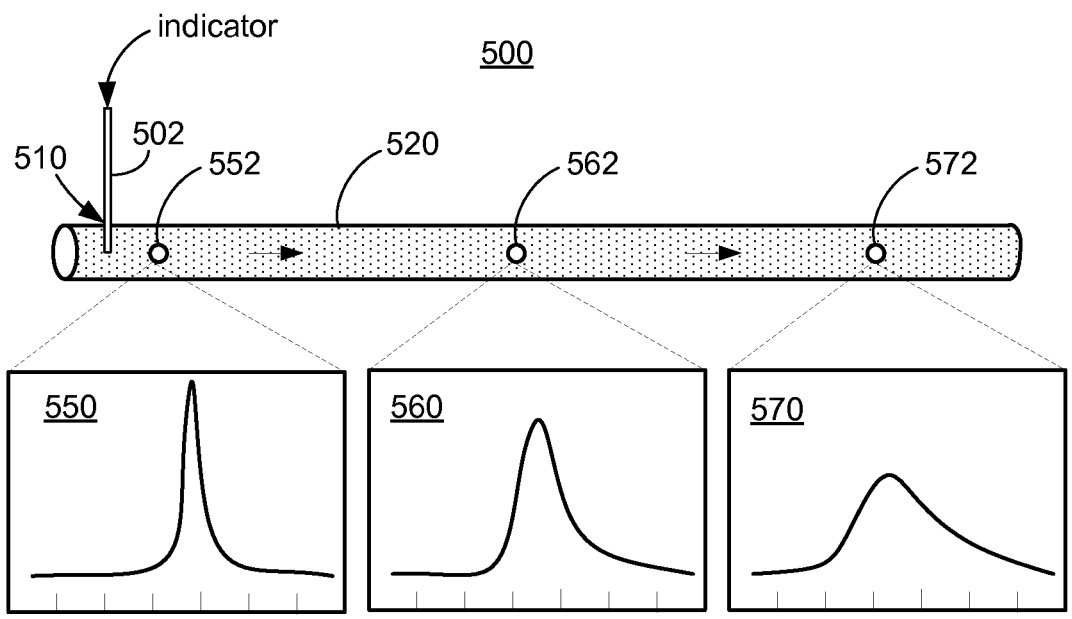
FIG. 5 shows an illustrative indicator arrangement, in accordance with some embodiments of the present disclosure.

FIG. 5 shows an illustrative indicator arrangement 500, in accordance with some embodiments of the present disclosure. In some embodiments, an indicator may be provided to the circulatory system of a subject to aid in determining one or more physiological parameters. For example, a saline solution may be injected into a subject's circulatory system at blood vessel site 510 using needle 502. Blood vessel site 510 may be located at any suitable portion of a subject's circulatory system such as a vein, an artery, a capillary, or other suitable location. For example, blood vessel site 510 may be a central vein of the subject. Portion 520 of the subject's circulatory system shown illustratively in FIG. 5 may include heart chambers, arteries, veins, capillaries, any other suitable parts of the circulatory system, or any combination thereof. As the indicator travels along portion 520, in the direction of the motion arrows, the concentration and/or temperature profile of may change. For example, panel 550 shows an illustrative dilution curve time series as detected at site 552, relatively near site 510. Panels 560 and 570 each show illustrative time series of dilution curves at sites 562 and 572, respectively, both downstream from site 552. The dilution curve shown in panel 560 is relatively flattened in time compared to the dilution curve shown in panel 550. The dilution curve shown in panel 570 is relatively flattened in time compared to the dilution curve shown in panel 560. The flattening may be due to diffusion and mixing of the indicator with the subject's blood. The area under the time series of panels 550, 560, and 570 may be, but need not be, the same and may depend on the indicator type, travel time, site location, and other suitable variables. The phrase "dilution curve" as used herein shall refer to a time series, continuous or discrete, indicative of dilutive effects of an indicator on the concentration of blood constituents and/or blood temperature. For example, a dilution curve may include a time series of concentration or changes thereof of a blood constituent, an indicator, or both. In a further example, a dilution curve may include a time series of temperature, or change in temperature, of blood of the subject at a monitoring site.

In some embodiments, an indicator may be introduced to a vena cava or other vein. A photoacoustic monitoring system may be used to non-invasively detect the presence of the indicator in an arterial vessel (e.g., pulmonary artery, brachial artery, carotid artery, aorta) of the subject. The blood travels from the venous system to the right atrium and then ventricle, from which it is pumped to the lungs via the pulmonary arteries. Transport of water and other substances between the lungs and blood vessels occurs at the lung tissue. Accordingly, lung water may diffuse to the blood stream, depending upon the chemical potential difference of water between the lung tissue and the blood stream. Oxygenated blood leaving the lung tissue and returning to the heart is pumped by the left atrium and ventricle to the body via the aorta and other suitable portions of the arterial system of the subject. Characteristics of a measured dilution curve may provide an indication of CO of the subject. The dilatory effects of the indicator in the blood may depend on the interaction in the lung tissue, and may provide an indication of parameters such as, for example, EVLW. Properties of the subject's vasculature may be determined based at least in part on the measured dilution curves.

Isotonic and Hypertonic Indicators

Figure 6:
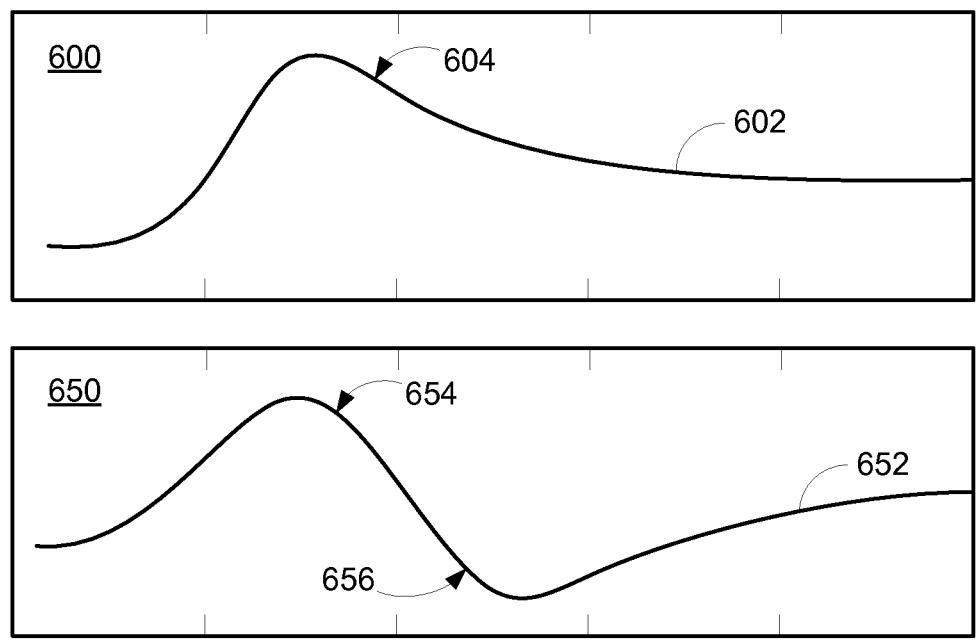
FIG. 6 shows illustrative dilution curves for isotonic and hypertonic saline indicators, in accordance with some embodiments of the present disclosure.

In some embodiments, more than one indicator may be introduced to the subject's circulatory system at the same time or in succession. For example, in some embodiments, an isotonic indicator (e.g., 0.9% w/v saline) and a hypertonic indicator (e.g., 5% w/v saline) may be introduced in succession, and respective dilution curves may be measured for both indicators. Shown in FIG. 6 are illustrative dilution curves 602 and 652 for isotonic and hypertonic saline indicators, respectively, in accordance with some embodiments of the present disclosure. The abscissa of each of illustrative plots 600 and 650 are shown in units of time, while the ordinate of each of illustrative plots 600 and 650 are shown in arbitrary units. In some embodiments, dilution curves such as, for example, dilution curves 602 and 652 may be time series in units of indicator concentration, tHb, temperature, photoacoustic signal, change in tHb, change in temperature, change in photoacoustic signal, or any other suitable units indicative of an indicator dilution response.

Plot 600 shows dilution curve 602 indicative of introduction of an isotonic indicator to a subject's bloodstream. Dilution curve 602 is unipolar, and exhibits a peak 604, followed by a gradual steadying to a steady-state value. Because the isotonic indicator includes water having a chemical potential approximately equal to that of, for example, water in the lung tissue, the net diffusion of the indicator out of the vessel is zero.

Plot 650 shows dilution curve 652 indicative of introduction of a hypertonic indicator to a subject's bloodstream. Dilution curve 652 is bipolar, and exhibits a peak 654, followed by a trough 656, and then a gradual steadying to a steady-state value. Because the hypertonic indicator includes water having a chemical potential less than that of, for example, lung tissue, the net diffusion of the indicator out of the vessel may be nonzero. Water diffuses from the lung tissue to the blood, due to the imbalanced chemical potential of water across the permeable lung/vessel interfaces. This interaction may reduce the chemical potential of water in the lung tissue. Peak 654 indicates the increased dilution due to the indicator and the water transferred from the lung in the bloodstream. Accordingly, as the bolus dose of indicator travels away from the lung tissue via the pulmonary vein, blood with reduced indicator content, upstream of the bolus dose, reaches the lung tissue. The chemical potential imbalance then reverses, and water diffuses to the lung tissue from the blood. Trough 656 indicates the decreased dilution due to the transport of water from the bloodstream to the lung tissue. In some circumstances, the effect of the indicator may be reduced as time progresses, due to mixing and/or bio-regulation, illustratively indicated by the gradual return of dilution curves 602 and 652 to a steady-state, or near steady-state, condition.

Figure 7:
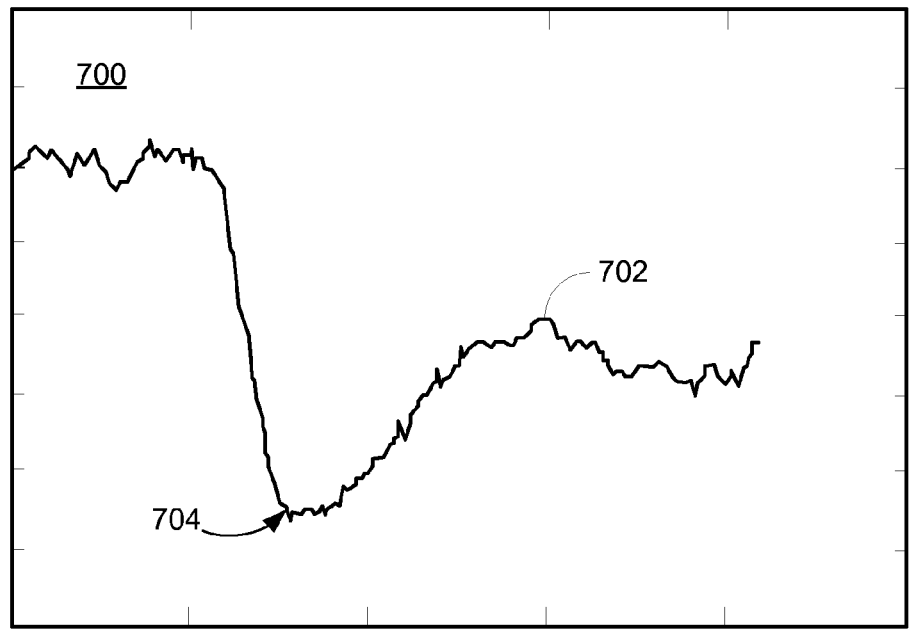
FIG. 7 shows an illustrative photoacoustic signal, including a response corresponding to an isotonic indicator, in accordance with some embodiments of the present disclosure.

FIG. 7 shows a plot 700 of an illustrative time domain photoacoustic signal 702, including a response corresponding to an isotonic indicator, in accordance with some embodiments of the present disclosure. Photoacoustic signal 702 may be a pre-processed and/or processed signal derived from the output of an acoustic detector. For example, photoacoustic signal 702 may include sample points corresponding to a maximum acoustic response for each light pulse (e.g., an acoustic pressure peak value), at a particular time lag corresponding to a particular spatial location (e.g., a particular blood vessel). The abscissa of plot 700 is shown in units of time, while the ordinate of plot 700 is shown in units proportional to voltage. A light source is used to provide a photonic signal to a first site of a circulatory system, causing a photoacoustic response of constituents in the circulating blood at that site. An acoustic detector is used to detect acoustic pressure signals caused by the photonic signal at the first site, and output photoacoustic signal 702. An isotonic indicator is injected as a bolus dose into the circulating blood at a second site. As the bolus dose travels past the first site, the hemoglobin concentration at the first site temporarily decreases. Trough 704 indicates the dilatory effects of the bolus dose of isotonic indicator. The acoustic detector detects a reduced acoustic pressure signal caused by the reduced hemoglobin concentration. The effect of the indicator may be detected as a trough in the acoustic pressure signal corresponding to the passing of the bolus dose through the first site. Note that photoacoustic signal 702 may be indicative of tHb, exhibiting a substantially steady-state baseline and trough 704 indicative of the presence of the indicator (e.g., a reduction of tHb via displacement by the indicator). Note that a plot of indicator concentration as a function of time may exhibit a peak, corresponding to a steady-state tHb value minus an instantaneous tHb value. A dilution curve may include either a peak or a trough depending upon the species monitored and the units used in calculation.

Figure 8:
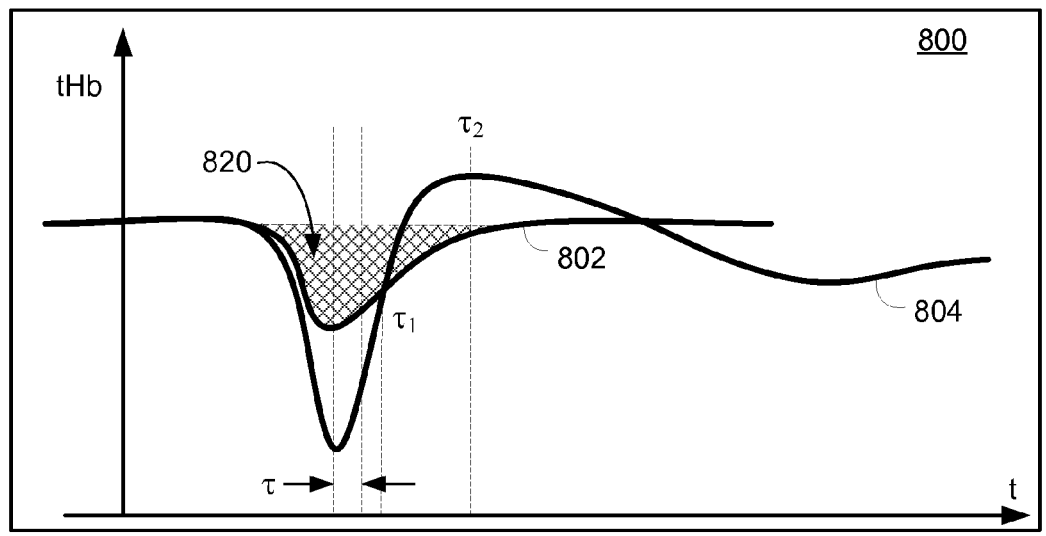
FIG. 8 shows an illustrative plot of total hemoglobin concentration as isotonic and hypertonic indicators pass a photoacoustic detection site, in accordance with some embodiments of the present disclosure.

FIG. 8 shows an illustrative plot 800 of two total hemoglobin concentration time series as respective isotonic and hypertonic indicators pass a photoacoustic detection site, in accordance with some embodiments of the present disclosure. The abscissa of plot 800 is shown in units of time, and the ordinate of plot 800 is shown in units of total hemoglobin concentration, although any suitable units may be used in accordance with the present disclosure. Time series 802 and 804 may be pre-processed and/or processed signals derived from the output of an acoustic detector. For example, time series 802 and 804 may each include sample points corresponding to a maximum acoustic response for each light pulse (e.g., an acoustic pressure peak value), at a particular time lag corresponding to a particular spatial location (e.g., a particular blood vessel). Time series 802 is total hemoglobin concentration as the isotonic indicator travels through the photoacoustic detection site. Alternatively, if the indicator concentration were shown rather than tHb, it may exhibit a peak rather than a trough, corresponding to the shaded area 820. Time series 804 is total hemoglobin concentration as the hypertonic indicator travels through the photoacoustic detection site. The variable t as shown in FIG. 8 represents time relative to each response, and not an absolute time scale. For example, the time origin for both responses may be zero, and they may be plotted on the same axis even though the indicators were introduced at different times. The variable τ as shown in FIG. 8 represents the mean transit time difference between the two responses.

In some embodiments, one or more characteristics may be derived from one or both responses. For example, the flow rate of a particular indicator may be formulated as shown by:

$$\dot{V}C_i = \dot{N} \quad (14)$$

where $\dot{V}$ is the volumetric flow rate of blood (e.g., volume/time, assumed here to be constant in time), $C_i$ is the concentration of indicator i (e.g., mole/volume, equivalent to the reduction in tHb using suitable assumptions), and $\dot{N}$ is the molar flow rate of molecule i (e.g., mole/time). Defining the cardiac output CO to be equal to volumetric flow rate $\dot{V}$, and referencing time series 802, the following Eq. 15 may be derived by integrating both sides of Eq. 14 in time:

$$CO = \frac{N}{A} \quad (15)$$

where cardiac output CO is proportional to the total isotonic indicator amount introduced N (e.g., moles, equivalent to the time integral of $\dot{N}$), and A is given by:

$$A = \int C_i dt \quad (16)$$

where A may be equivalent to the area 820 bounded by time series 802 and the steady tHb value. If the ordinate of plot 800 were shown in units other than concentration, a constant of proportionality may be required in Eq. 16 if time series values are used. Under some circumstances, cardiac output may be equal to the ratio of isotonic indicator amount introduced and the area bounded by the time series and the steady tHb value, while in other circumstances the equality of Eqs. 15-16 may be replaced by the proportionality symbol ∝ (e.g., to account for density differences). Area A is an illustrative example of a characteristic derived from a response to an indicator.

In a further example, EVLW may be formulated based on both time series 802 and 804, as shown by Eq. 17:

$$EVLW = CO * \Delta\tau_{MT} \quad (17)$$

where CO is the cardiac output, and $\Delta\tau_{MT}$ is the mean transit time difference between the isotonic and hypertonic indicator dilution curves. The mean transit time of an indicator dilution curve may be based on any suitable reference point of the curve. The mean transit time for a dilution curve may be calculated using Eq. 18:

$$\tau_{MT} = \tau_0 + \frac{\int C_i * (t - \tau_0) dt}{\int C_i dt} \quad (18)$$

where $\tau_0$ is the time after introduction of the indicator when the indicator is detected at the PA monitoring site, and $C_i$ is the indicator concentration.

In a further example, a vascular permeability metric vp may be defined as:

$$vp = \tau_2 - \tau_1 \quad (19)$$

where $\tau_2$ is the peak time of time series 804, and $\tau_1$ is the time where time series 802 and 804 cross. In some circumstances, vascular permeability may provide an indication and/or measure of the possibility of a capillary leak and the possibility of fluid accumulating outside of the blood vessels.

In a further example, EVLW may be determined based on an osmotic response (e.g., the transfer of water and salt between the blood and lungs due to a chemical potential difference) of the subject using an isotonic and hypertonic indicator. EVLW may be determined using the following Eq. 20, for the hypertonic indicator:

$$EVLW = \frac{\prod_b \left(\frac{\Delta n_3}{c} - \Delta EVLW_3\right)}{\Delta \prod_{b,3}} \quad (20)$$

where $\Pi_b$ is the steady state osmolarity of the subject's blood (e.g., before introduction of the hypertonic indicator), $\Delta \Pi_{b13}$ is the change in the osmolarity of subject's blood at time $\tau_3$, $\Delta n_3$ is the total amount of salt transferred from the subject's blood to the subject's lungs at time $\tau_3$, c is the concentration of solutes in the EVLW, and $\Delta EVLW_3$ is the total change in extravascular lung water at time $\tau_3$. The time $\tau_3$ is the time, referenced to zero at the beginning of the response, when the EVLW and blood have the same osmotic pressure for the hypertonic indicator.

Thermo-Dilution Indicators

In some embodiments, a thermo-dilution indicator may be introduced to the subject's circulatory system at a suitable location. For example, in some embodiments, a saline solution having a temperature less than that of a subject's blood may be introduced, and one or more dilution curves may be measured at one or more respective locations in the subject's vasculature. The Grüneisen parameter of the subject's blood may depend on temperature linearly according to the illustrative empirical relation:

$$\Gamma = mT + b \quad (21)$$

where m is a slope and b is an intercept. Accordingly, Eq. 1 may be rewritten as follows:

$$p(z,T) = \Gamma(T)\mu_a \phi(z). \quad (22)$$

Showing that as the temperature at the photoacoustic monitoring site changes, the acoustic pressure signal may change accordingly. Introduction of thermo-dilution indicator may be used to determine cardiac output, ITCV, PCV, and/or GEDV, for example.

In some embodiments, cardiac output CO may be calculated using:

$$CO = K \frac{(T_{b,0} - T_{i,0}) V_i}{\int (T_{b,0} - T_b(t)) dt} \quad (23)$$

where K is a proportionality constant (e.g., including the effects of specific gravity and heat capacity of blood and/or the indicator), $T_{b,0}$ is the initial blood temperature at the time and site of injection, $T_{i,0}$ is the initial indicator temperature, $V_i$ is the volume of injected indicator, and $T_b(t)$ is the blood temperature at time t, as measured using the photoacoustic technique. Note that the moles of injected indicator may be used rather than $V_i$ in some cases, with a suitable adjustment of the proportionality constant K to include the indicator concentration (e.g., mole/volume). In some embodiments, an expression such as, for example, Eq. 22 may be solved for temperature as a function of photoacoustic signal, and the function may include one or more parameters that may depend on tissue properties and/or system properties. Accordingly, a photoacoustic monitoring system (e.g., system 10 of FIGS. 1-2 or system 300 of FIG. 3) may use one or more references such as pre-defined constants, reference PA signals, correlations, or look-up tables to determine a temperature, or change thereof, from a detected acoustic pressure signal. In some embodiments, a photoacoustic monitoring system may be calibrated for a particular subject or particular monitoring site of a subject. In some embodiments, a photoacoustic monitoring system may use a thermo-dilution indicator response and a body-temperature hemo-dilution indicator response (e.g., to de-couple the temperature and concentration effects) to determine a temperature or change thereof.

In some embodiments, ITCV may be calculated using:

$$ITCV = CO * \tau_{MT} \quad (24)$$

where CO is cardiac output (e.g., which may be calculated using Eq. 23), and $\tau_{MT}$ is the mean transit time of the thermo-dilution curve. The mean transit time for a thermo-dilution indicator may be calculated using:

$$\tau_{MT} = \tau_0 + \frac{\int (T_{b,0} - T_b(t)) * (t - \tau_0) dt}{\int (T_{b,0} - T_b(t)) dt} \quad (25)$$

where $\tau_0$ is the time after introduction of the indicator when the indicator is detected at the PA monitoring site, and $(T_{b,0} - T_b(t))$ is the difference in initial and instantaneous blood temperature of the thermo-dilution curve. In some embodiments, in which a thermo-dilution indicator may be used, a circulatory volume may be equivalent to a thermal volume.

In some embodiments, PCV may be calculated using:

$$PCV = CO * \tau_{DS} \quad (26)$$

where CO is the cardiac output, and $\tau_{DS}$ is the downslope time of the thermo-dilution curve. In some embodiments, the downslope time may be determined as the time interval of the linear decay of the indicator response (e.g., downslope of a peak), from about 80% of the peak value to about 20% of the peak value. In some circumstances, downslope time may provide an indication and/or measure of the washout of the indicator, which may depend on the volume which the indictor dilutes.

In some embodiments, GEDV may be calculated using:

$$GEDV = ITCV - PCV \quad (27)$$

which may be indicative of the blood volume included in the ITCV.

In some embodiments, EVLW may be calculated using:

$$EVLW = ITCV - ITBV \quad (28)$$

where ITBV may be calculated from GEDV, which may be calculated using Eq. 27. For example, ITBV may be directly proportional to GEDV, with a proportionality constant of order one (e.g., a constant of 1.25). Accordingly, in some embodiments, ITCV, PCV, GEDV, ITBV, and EVLW may be determined based on a thermo-dilution indicator.

Hemo-Dilution and Thermo-Dilution Indicators

In some embodiments, both a thereto-dilution indicator and a hemo-dilution indicator may be introduced to the subject's circulatory system at suitable locations and times. For example, in some embodiments, a saline solution having a temperature less than that of a subject's blood may be introduced, and a dye indicator such as indocyanine green dye may be introduced. Accordingly, two or more dilution curves may be measured at one or more locations in the subject's vasculature, indicative of the hemo-dilution and thermo-dilution indicators. Any of the properties that may be calculated using Eqs. 21-27 may be calculated using the thermo-dilution indicator. In some embodiments, ITBV may be calculated using the hemo-dilution curve, as shown by:

$$ITBV = CO * \tau_{MT} \quad (29)$$

where CO is the cardiac output (e.g., calculated using Eq. 15 or 23), and $\tau_{MT}$ is the mean transit time of the hemo-dilution curve (e.g., calculated using Eq. 18).

In some embodiments, EVLW may be calculated from the thermo-dilution curve and hemo-dilution curve using:

$$EVLW = ITCV - ITBV \quad (30)$$

wherein ITCV may be calculated from the thermo-dilution curve (e.g., using Eq. 24), and ITBV may be calculated from the hemo-dilution curve (e.g., using Eq. 29).

Any of the thermal-dilution and Nemo-dilution techniques, using one or more indicators, including the use of an isotonic and a hypertonic indicator, may be used alone or in combination with other techniques. Accordingly, any of Eqs. 14-30 may be used alone or in concert to determine physiological information of a subject such as a physiological parameter. FIGS. 9-12 include flowcharts of illustrative steps for implementing the aforementioned techniques. In some embodiments, other information may be determined based on indicator dilution techniques (e.g., using an indocyanine green indicator, liver function and/or total blood volume may be determined).

Figure 9:
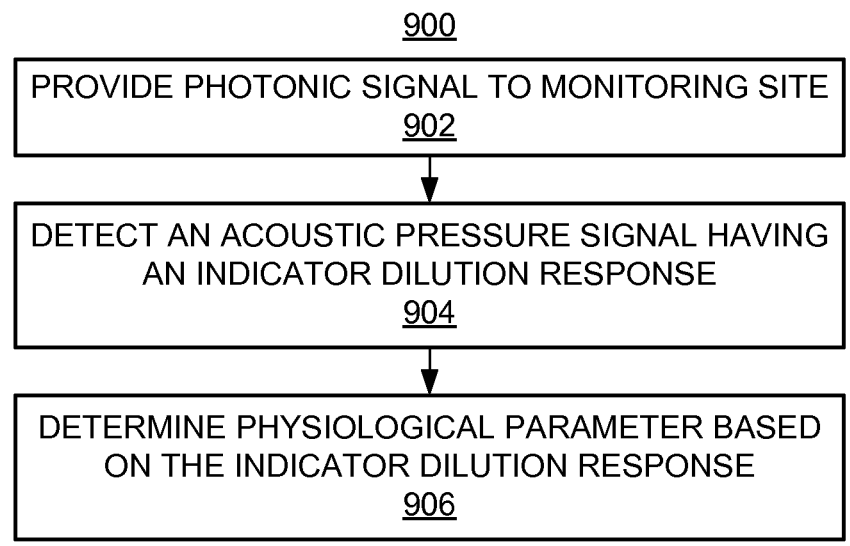
FIG. 9 is a flow diagram of illustrative steps for determining a physiological parameter from an acoustic pressure signal having an indicator dilution response, in accordance with some embodiments of the present disclosure.

FIG. 9 is a flow diagram 900 of illustrative steps for determining a physiological parameter from an acoustic pressure signal having an indicator dilution response, in accordance with some embodiments of the present disclosure.

Step 902 may include a suitable light source (e.g., light source 16 of system 10) of system 300 providing a photonic signal to a subject. The light source may be a pulsed light source, continuous wave light source, any other suitable light source, or any combination thereof. In some embodiments, modulator 44 may be used to modulate the photonic signal of the light source. In some embodiments, the photonic signal may be focused or otherwise spatially modulated. For example, the photonic signal may be focused on or near a blood vessel, which may contain blood that absorbs at least some of the photonic signal, causing a relatively stronger photoacoustic response and accordingly a stronger photoacoustic signal than surrounding tissue.

Step 904 may include system 300 detecting an acoustic pressure signal having an indicator response. In some embodiments, an acoustic detector such as, for example, an ultrasound detector of system 300 may detect the acoustic pressure signal. The acoustic detector may output an electrical signal to suitable processing equipment of system 300. The acoustic pressure signal may be detected as a time series (e.g., in the time domain or sample number domain), and processed as a time series, as a spectral series (e.g., in the frequency domain), any other suitable series, or any combination thereof. In some embodiments, pre-processor 320 may pre-process the detected acoustic pressure signal. For example, pre-processor 320 may perform filtering, amplifying, de-multiplexing, de-modulating, sampling, smoothing, any other suitable pre-processing, or any combination thereof. The acoustic pressure signal may include a hemo-dilution and/or thermo-dilution response characterized by a temporal peak or trough in concentration, temperature, any other suitable property of the monitoring site, any changes thereof, or any combination thereof. In some embodiments, processor 312 may use a peak finding technique to locate a peak and/or trough. For example, processor 312 may locate a maximum or minimum in the photoacoustic signal, locate a zero in the first derivative of the photoacoustic signal, perform any other suitable peak finding technique, or any combination thereof. The peak finding technique may operate on only a subset of the photoacoustic signal. For example, the peak finding algorithm may only start looking for a peak and/or trough after a predetermined time or sample number from the introduction of the indicator. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal.

Step 906 may include system 300 determining one or more physiological parameters of the subject based at least in part on the indicator dilution response detected at step 904. Physiological parameters may include hemoglobin, blood oxygen saturation, CO, ITBV, ITCV, GEDV, PCV, EVLW, any other suitable hemodynamic parameters, any other suitable physiological parameters, any physiological modulations thereof, or any combination thereof. In some embodiments, step 906 may include processor 312 determining one or more characteristics based at least in part on the indicator dilution response. Processor 312 may determine characteristics such as particular values of the acoustic pressure signal or values of a signal derived thereof (e.g., a tHb value), areas under or between signals (e.g., integrals), temporal values or differences (e.g., as shown by Eqs. 18, 19, and 25), any other suitable characteristics, or any combination thereof. For example, processor 312 may calculate one or more physiological parameters using any or all of Eqs. 14-16, 18, and 23-29, based on a detected indicator dilution response. In some embodiments, an acoustic pressure signal may be influenced by arterial pulsations and/or respiratory synchronous variations, or other biological modulations. In some such embodiments, system 300 may use a spectral filter (e.g., a notch filter, a high-pass filter) to reduce the influence of these biological modulations that typically occur over larger time scales than the time scales of an acoustic pressure signal. For example, system 300 may apply a spectral filter to a photoacoustic signal derived from an acoustic pressure signal, to filter out pulsatile components.

Figure 10:
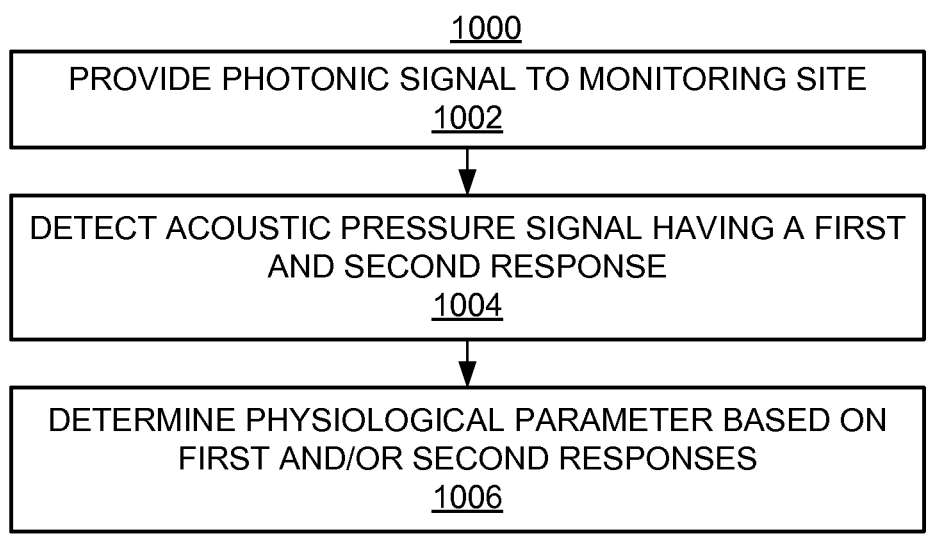
FIG. 10 is a flow diagram of illustrative steps for determining a physiological parameter from an acoustic pressure signal having a first and a second response, in accordance with some embodiments of the present disclosure.

FIG. 10 is a flow diagram 1000 of illustrative steps for determining a physiological parameter from an acoustic pressure signal having a first and a second response, in accordance with some embodiments of the present disclosure.

Step 1002 may include a suitable light source (e.g., light source 16 of system 10) of system 300 providing a photonic signal to a subject, at a monitoring site. The light source may be a pulsed light source, continuous wave light source, any other suitable light source, or any combination thereof. In some embodiments, modulator 44 may be used to modulate the photonic signal of the light source. In some embodiments, the photonic signal may be focused or otherwise spatially modulated. For example, the photonic signal may be focused on or near a blood vessel, which may contain blood that absorbs at least some of the photonic signal, causing a relatively stronger photoacoustic response and accordingly a stronger photoacoustic signal than surrounding tissue. In some embodiments, step 1002 may include providing the photonic signal at two particular times to monitor the respective first and second responses. For example, the photonic signal of step 1002 may be provided in response to the introduction of an indicator, at a suitable time to monitor the response at the monitoring site of the subject. In some embodiments, step 1002 may include providing the photonic signal steadily, and using processor equipment to locate the response in the time series.

Step 1004 may include system 300 detecting an acoustic pressure signal having a first and a second response. In some embodiments, an acoustic detector such as, for example, an ultrasound detector of system 300 may detect the acoustic pressure signal. The acoustic detector may output an electrical signal to suitable processing equipment of system 300. The acoustic pressure signal may be detected as a time series (e.g., in the time domain or sample number domain), and processed as a time series, as a spectral series (e.g., in the frequency domain), any other suitable series, or any combination thereof. In some embodiments, pre-processor 320 may pre-process the detected acoustic pressure signal. For example, pre-processor 320 may perform filtering, amplifying, de-multiplexing, de-modulating, sampling, smoothing, any other suitable pre-processing, or any combination thereof. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal. The photoacoustic signal may include a first and a second response, which may be hemo-dilution and/or thermo-dilution responses. The responses may be characterized by a temporal peak or trough in the photoacoustic signal, a concentration time series derived thereof, a temperature time series derived thereof, any other suitable signal, any changes thereof, or any combination thereof. In some embodiments, processor 312 may use a peak finding technique to locate a peak and/or trough. For example, processor 312 may locate a maximum or minimum in the photoacoustic signal, locate a zero in the first derivative of the photoacoustic signal, perform any other suitable peak finding technique, or any combination thereof. The peak finding technique may operate on only a subset of the photoacoustic signal. For example, the peak finding algorithm may only start looking for a peak and/or trough after a predetermined time or sample number from the introduction of the respective indicator.

Step 1006 may include system 300 determining one or more physiological parameters of the subject based at least in part on the first and/or second responses detected at step 1004. Physiological parameters may include hemoglobin, blood oxygen saturation, CO, ITBV, ITCV, GEDV, PCV, EVLW, any other suitable hemodynamic parameters, any other suitable physiological parameters, any physiological modulations thereof, or any combination thereof. In some embodiments, step 1004 may include processor 312 determining one or more characteristics based at least in part on the first and/or second responses. Processor 312 may determine characteristics such as particular values of the acoustic pressure signal or values of a signal derived thereof (e.g., a tHb value), areas under or between signals (e.g., integrals), temporal values or differences (e.g., as shown by Eqs. 18, 19, and 25), any other suitable characteristics, or any combination thereof. For example, processor 312 may calculate one or more physiological parameters using any or all of Eqs. 14-20, and 23-30, based on detected first and/or second responses. More particularly, processor 312 may calculate EVLW from an isotonic indicator dilution response and a hypertonic indicator dilution response using Eq. 17. Also more particularly, processor 312 may calculate ITBV, ITCV, and EVLW from a hemo-dilution response and a thermo-dilution response using Eqs. 29-30.

Figure 11:
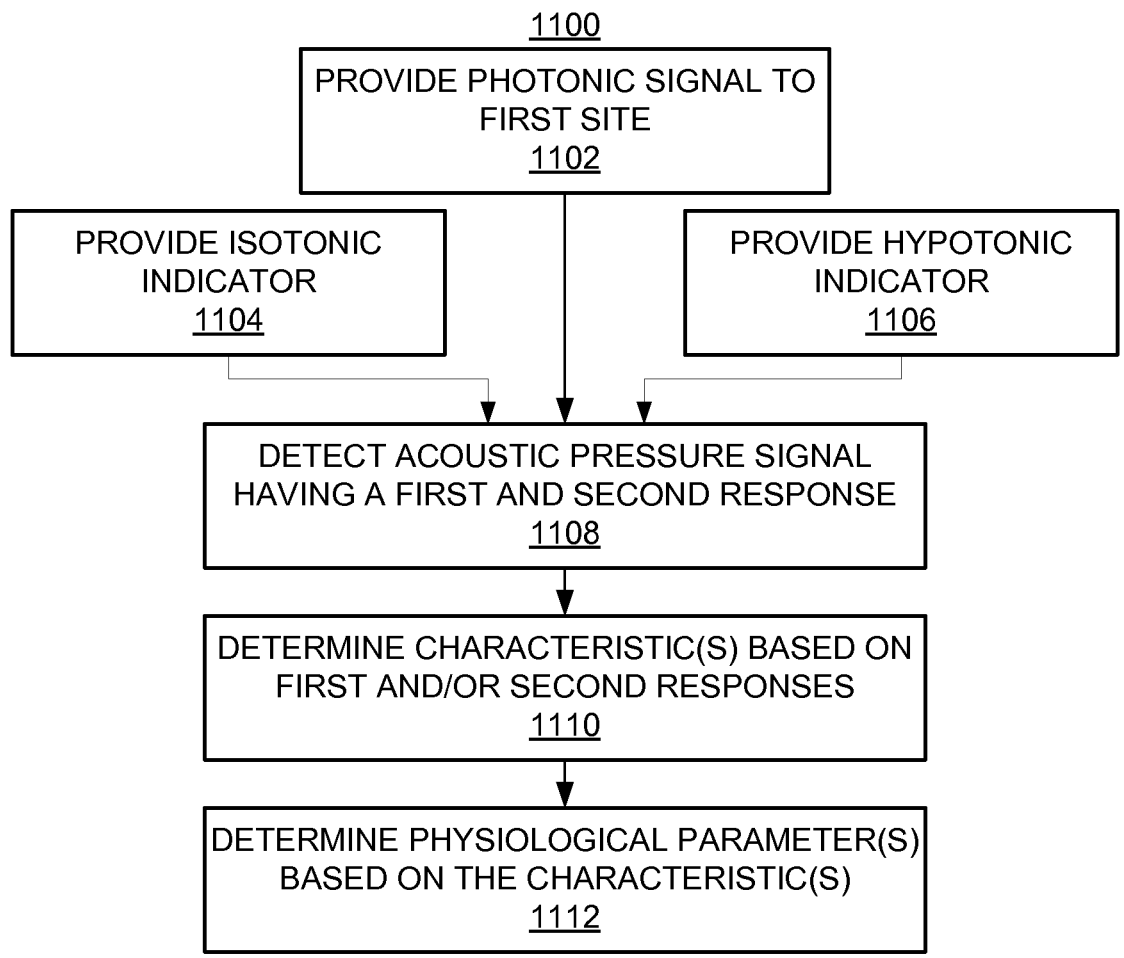
FIG. 11 is a flow diagram of illustrative steps for determining a physiological parameter from an acoustic pressure signal having a first and a second response, corresponding to respective hypertonic and isotonic indicators, in accordance with some embodiments of the present disclosure.

FIG. 11 is a flow diagram 1100 of illustrative steps for determining a physiological parameter from an acoustic pressure signal having a first and second response, corresponding to respective isotonic and hypertonic indicators, in accordance with some embodiments of the present disclosure.

Step 1102 may include a suitable light source (e.g., light source 16 of system 10) of system 300 providing a photonic signal to a subject, at a first site. The light source may be a pulsed light source, continuous wave light source, any other suitable light source, or any combination thereof. In some embodiments, modulator 44 may be used to modulate the photonic signal of the light source. In some embodiments, the photonic signal may be focused or otherwise spatially modulated.

Step 1104 may include providing an isotonic indicator to a subject at a second site, at a first time. In some embodiments, a bolus dose of the isotonic indicator may be injected using a hypodermic needle, inserted into a blood vessel of the subject. The bolus dose may include, for example, a volume on the order of ten milliliters. Such a dose applied to the central vein may dilute the blood inside the heart up to ten percent. In some embodiments, the bolus dose of isotonic indicator may be introduced at substantially the same temperature of the subject at the second site. In some embodiments, the bolus dose of isotonic indicator may be introduced at a temperature different from the temperature of the subject at the second site (e.g., the bolus dose may be relatively warmer or cooler).

Step 1106 may include providing a hypertonic indicator to a subject at or near the second site, at a second time. In some embodiments, a bolus dose of the hypertonic indicator may be injected using a hypodermic needle, inserted into a blood vessel of the subject. The bolus dose may include, for example, a volume on the order of ten milliliters. The second time may be before or after the first time (i.e., the introduction of the isotonic and hypertonic indicators may be in any suitable order). In some embodiments, the bolus dose of hypertonic indicator may be introduced at substantially the same temperature of the subject at the second site. In some embodiments, the bolus dose of hypertonic indicator may be introduced at a temperature different from the temperature of the subject at the second site (e.g., the bolus dose may be relatively warmer or cooler). The bolus dose of hypertonic indicator may be introduced at a temperature the same as, or different from, the temperature of the bolus dose of isotonic indicator of step 1104.

Step 1108 may include system 300 detecting an acoustic pressure signal having a first and a second response, corresponding to the isotonic and hypertonic indicators. In some embodiments, an acoustic detector such as, for example, an ultrasound detector of system 300 may detect the acoustic pressure signal. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal. The acoustic detector may output an electrical signal to suitable processing equipment of system 300. In some embodiments, the first and second responses may be detected as peaks or troughs in the photoacoustic signal, distinguishable from a baseline photoacoustic signal.

Step 1110 may include system 300 determining one or more characteristics based at least in part on the first and/or second response. Processor 312 may determine characteristics such as particular values of the acoustic pressure signal or values of a signal derived thereof, areas under or between dilution curves, temporal values or differences, any other suitable characteristics, or any combination thereof. For example, a mean transit time may be determined using any of Eqs. 18 or 25. In a further example, a mean transit time difference may be determined using Eq. 18. In a further example, an integral may be determined using Eq. 16. In a further example, a crossing time may be determined such as variable $\tau_1$ used in Eq. 19. In a further example, a time associated with a peak value may be determined such as variable $\tau_2$ used in Eq. 19. In a further example, a time difference may be determined using Eq. 19.

Step 1112 may include system 300 determining one or more physiological parameters of the subject based at least in part on the one or more characteristics of step 1110. Physiological parameters may include hemoglobin, blood oxygen saturation, CO, ITBV, ITCV, GEDV, PCV, EVLW, any other suitable hemodynamic parameters, any other suitable physiological parameters, any physiological modulations thereof, or any combination thereof. For example, processor 312 may calculate one or more physiological parameters based on suitable characteristics using any or all of Eqs. 14-20.

Figure 12:
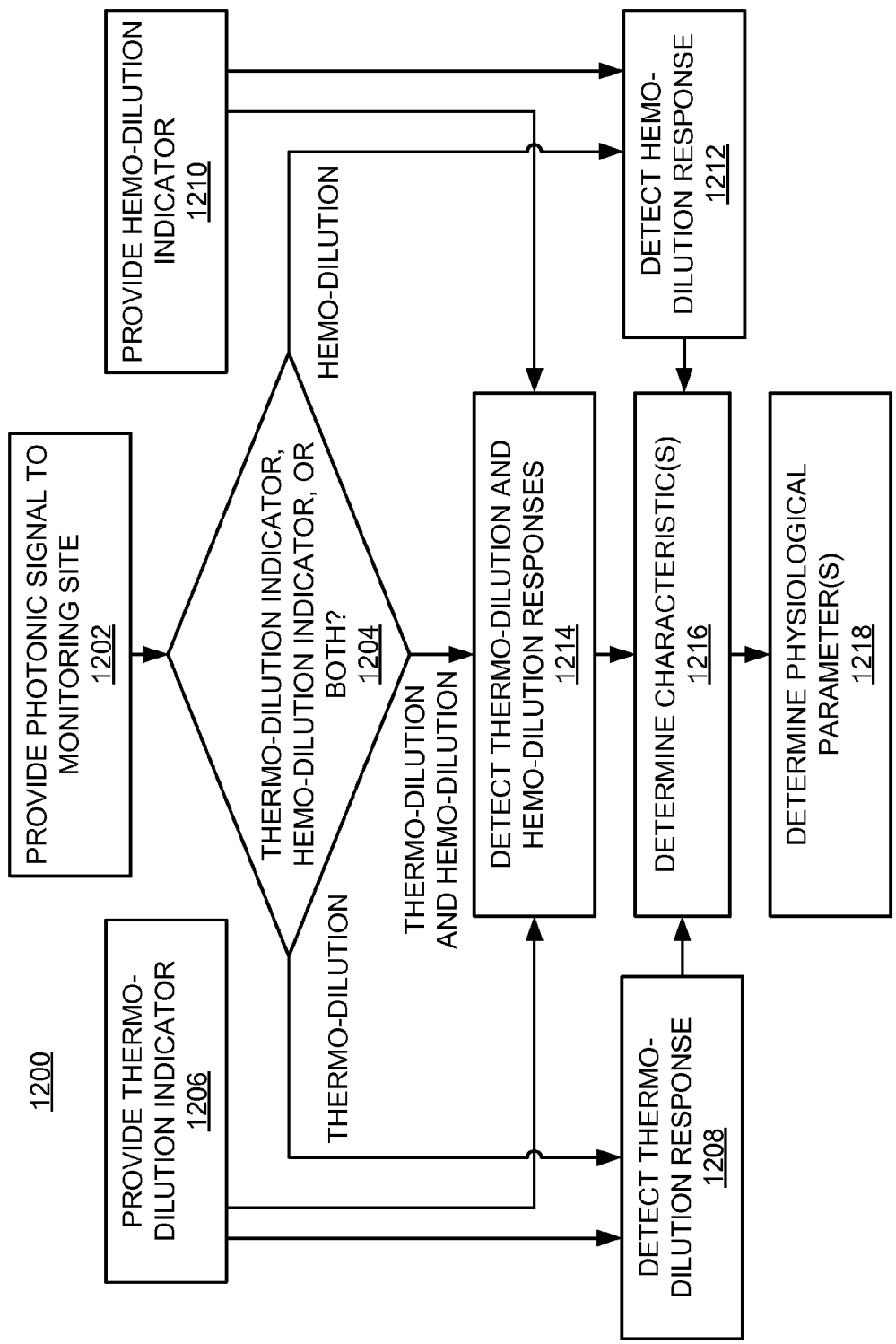
FIG. 12 is a flow diagram of illustrative steps for determining a physiological parameter from an acoustic pressure signal having a hemo-dilution and/or thermo-dilution response, in accordance with some embodiments of the present disclosure.

FIG. 12 is a flow diagram 1200 of illustrative steps for determining a physiological parameter from an acoustic pressure signal having a Nemo-dilution and/or thermo-dilution response, in accordance with some embodiments of the present disclosure.

Step 1202 may include a suitable light source (e.g., light source 16 of system 10) of system 300 providing a photonic signal to a subject, at a monitoring site. The light source may be a pulsed light source, continuous wave light source, any other suitable light source, or any combination thereof. In some embodiments, modulator 44 may be used to modulate the photonic signal of the light source. In some embodiments, the photonic signal may be focused or otherwise spatially modulated.

Step 1204 may include determining which indicators are to be introduced to the subject. One or more thermo-dilution indicators, one or more hemo-dilution indicators, or combinations thereof, may be introduced to the subject. In some embodiments, system 300 may determine which indicators to introduce to the subject. For example, in order to determine a particular physiological parameter, system 300 may determine that particular indicator(s) are required. In some embodiments, step 1204 may be performed by a user, who may input one or more commands (e.g., selections from a pull-down menu, entry of a text indication) into a suitable user interface (e.g., user inputs 56 of system 10). In some embodiments, system 300 may be configured to detect a particular response (e.g., thermo-dilution or hemo-dilution), and accordingly step 1204 need not be performed because no determination is required.

Step 1206 may include providing one or more thermo-dilution indicators to the subject at an indicator site, and then system 300 detecting a resulting thermo-dilution response of an acoustic pressure signal at step 1208 based at least in part on the photonic signal of step 1202. In some embodiments, a bolus dose of the thermo-dilution indicator may be injected using a hypodermic needle, inserted into a blood vessel of the subject. The bolus dose may include, for example, a volume on the order of ten milliliters. In some embodiments, the bolus dose of thermo-dilution indicator may be introduced at a temperature different from the temperature of the subject at the indicator site (e.g., the bolus dose may be relatively warmer or cooler). The thermo-dilution indicator may be an isotonic indicator, a hypertonic indicator, a hypertonic indicator, a dye indicator, any other suitable indicator, or any combination thereof. In some embodiments, an acoustic detector such as, for example, an ultrasound detector of system 300 may detect the acoustic pressure signal at step 1208. The acoustic detector may output an electrical signal to suitable processing equipment of system 300. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal. In some embodiments, the thermo-dilution response may be detected as a peak or trough in the photoacoustic signal, distinguishable from a baseline photoacoustic signal.

Step 1210 may include providing one or more hemo-dilution indicators to the subject, and then system 300 detecting a resulting hemo-dilution response of an acoustic pressure signal at step 1212 based at least in part on the photonic signal of step 1202. In some embodiments, a bolus dose of the hemo-dilution indicator may be injected using a hypodermic needle, inserted into a blood vessel of the subject. The bolus dose may include, for example, a volume on the order of ten milliliters. The bolus dose of hemo-dilution indicator may be, but need not be, introduced at the same temperature as the temperature of the subject at the indicator site. The hemo-dilution indicator may be an isotonic indicator, a hypertonic indicator, a hypertonic indicator, a dye indicator, any other suitable indicator, or any combination thereof. In some embodiments, an acoustic detector such as, for example, an ultrasound detector of system 300 may detect the acoustic pressure signal at step 1212. The acoustic detector may output an electrical signal to suitable processing equipment of system 300. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal. In some embodiments, the hemo-dilution response may be detected as a peak or trough in the photoacoustic signal, distinguishable from a baseline photoacoustic signal.

Step 1214 may include system 300 detecting a thermo-dilution response and a Nemo-dilution response of an acoustic pressure signal based at least in part on the photonic signal of step 1202, resulting from respective thermo-dilution and Nemo-dilution indicators provided at steps 1206 and 1210. In some embodiments, bolus doses of the thermo-dilution and hemo-dilution indicators may be injected using one or more hypodermic needles, inserted into one or more blood vessels (or sites thereof) of the subject. Each bolus dose may include, for example, a volume on the order of ten milliliters. In some embodiments, an acoustic detector such as, for example, an ultrasound detector of system 300 may detect the acoustic pressure signal at step 1208. The acoustic detector may output an electrical signal to suitable processing equipment of system 300. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal. In some embodiments, the thermo-dilution and hemo-dilution responses may be detected as peaks or troughs in the photoacoustic signal, distinguishable from a baseline photoacoustic signal. In some embodiments, the thermo-dilution indicator and hemo-dilution indicator may be introduced to the subject at different times and/or locations. For example, a particular time interval between the thermo-dilution and hemo-dilution indicators may be used to prevent mixing of the indicators and corresponding composite effects.

Step 1216 may include system 300 determining one or more characteristics based at least in part on the detected responses of any of steps 1208, 1212, and 1214. In some embodiments, the one or more characteristics may depend on the type of indicator that is provided (e.g., at steps 1206 and/or 1210). Characteristics may include particular values of the acoustic pressure signal or values of a signal derived thereof (e.g., a photoacoustic signal), areas under or between dilution curves, temporal values or differences, any other suitable characteristics, or any combination thereof. For example, one or more thermo-dilution indicators may be used, and the one or more characteristics may include a mean transit time (e.g., as included in Eqs. 24 and 25), a downslope time (e.g., as included in Eq. 26), and an integral of a portion of a dilution curve (e.g., as included in Eq. 23). In a further example, one or more hemo-dilution indicator may be used, and the one or more characteristics may include a mean transit time (e.g., as included in Eqs. 18 and 29), a time difference (e.g., as included in Eqs. 17 and 19), and an integral of a portion of a dilution curve (e.g., as included in Eq. 16). In a further example, a thermo-dilution indicator and a hemo-dilution indicator may be used, and the one or more characteristics may include a mean transit time (e.g., as included in Eqs. 18, 24, 25 and 29), a downslope time (e.g., as included in Eq. 26), a time difference (e.g., as included in Eqs. 17, 19 and 23), and an integral of a portion of a dilution curve (e.g., as included in Eq. 23).

Step 1218 may include system 300 determining one or more physiological parameters of the subject based at least in part on the one or more characteristics of step 1216. Physiological parameters may include hemoglobin, blood oxygen saturation, CO, ITBV, ITCV, GEDV, PCV, EVLW, any other suitable hemodynamic parameters, any other suitable physiological parameters, any physiological modulations thereof, or any combination thereof. For example, processor 312 may calculate one or more physiological parameters based on suitable characteristics using any or all of Eqs. 14-20 and 23-30.

In the foregoing flowcharts, an acoustic pressure signal having one or more indicators is detected. In some embodiments, the system (e.g., system 300) may continuously detect the acoustic pressure signal and continuously analyze the photoacoustic signal to identify the one or more indicator responses. In some embodiments, the system may only detect and analyze the acoustic pressure signal in response to a user input. For example, the user may press a key on the monitor shortly before the one or more indicators are injected. In some embodiments, the system may be communicatively coupled to the injection apparatus and therefore may automatically know when the one or more indicators are injected and when to detect the acoustic pressure signal. For example, the injection apparatus may transmit a signal to the system each time there is an injection. As another example, the system may control the injection apparatus and instruct the injection apparatus when to perform an injection.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A system for determining a value of the physiological parameter of a subject, the system comprising:
    a light source configured to provide a photonic signal to a first blood vessel site of the subject;
    an acoustic detector configured to detect an acoustic pressure signal from the first blood vessel site, wherein the acoustic pressure signal is caused by absorption of at least some of the photonic signal by one or more constituents at the first blood vessel site, and wherein the acoustic pressure signal comprises:
        a first acoustic pressure response based on an isotonic indicator provided to a second blood vessel site at a first time, and
        a second acoustic pressure response based on a hypertonic indicator provided to the second blood vessel site at a second time, wherein the first time and the second time are during the same clinical session; and
    processing equipment configured to determine a value of the physiological parameter of the subject based on the first response and the second response.

2. The system of claim 1, wherein the second blood vessel site comprises a site of a vein of the subject.

3. The system of claim 1, wherein the first blood vessel site comprises a site of a pulmonary artery of the subject.

4. The system of claim 1, wherein the first blood vessel site comprises a site of the aorta of the subject.

5. The system of claim 1, wherein the physiological parameter comprises cardiac output.

6. The system of claim 1, wherein the physiological parameter comprises extravascular lung water.

7. The system of claim 1, wherein the isotonic indicator comprises a saline solution having a concentration of about nine grams of sodium per liter of water.

8. The system of claim 1, wherein the hypertonic indicator comprises a saline solution having a concentration of about fifty grams of sodium per liter of water.

9. The system of claim 1, wherein at least one of the isotonic indicator and the hypertonic indicator comprises a dye indicator.

10. The system of claim 1, wherein the processing equipment is further configured to:
    generate a dilution curve based at least in part on at least one of the first response and the second response; and
    determine the physiological parameter of the subject further based at least in part on a time integral of the dilution curve.

11. The system of claim 1, wherein the physiological parameter comprises a pulse rate, a blood pressure, an arterial blood oxygen saturation, a venous blood oxygen saturation, an oxygenated hemoglobin concentration, a deoxygenated hemoglobin concentration, or any combination thereof.

12. A system for determining a value of a physiological parameter of a subject, the system comprising:
    a light source configured to provide a photonic signal to a site of a pulmonary artery or an aorta of a subject;
    one or more acoustic detectors configured to detect an acoustic pressure signal from the site of the pulmonary artery or the aorta of the subject, wherein the acoustic pressure signal is caused by the absorption of a portion of the photonic signal by the pulmonary artery or the aorta, and wherein the acoustic pressure signal comprises:
        a first acoustic pressure response based on an isotonic indicator provided to a site of a vein of the subject at a first time, and
        a second acoustic pressure response based on a hypertonic indicator provided to the site of the vein of the subject at a second time, wherein the first time and the second time are during the same clinical session; and
    processing equipment configured to determine a value of the physiological parameter of the subject based on the first response and the second response.

13. The system of claim 12, wherein the physiological parameter comprises cardiac output.

14. The system of claim 12, wherein the physiological parameter comprises extravascular lung water.

15. The system of claim 12, wherein the isotonic indicator comprises a saline solution having a concentration of about nine grams of sodium per liter of water.

16. The system of claim 12, wherein the hypertonic indicator comprises a saline solution having a concentration of about fifty grams of sodium per liter of water.

17. The system of claim 12, wherein at least one of the isotonic indicator and the hypertonic indicator comprises a dye indicator.

18. The system of claim 12, wherein the processing equipment is further configured to:
   generate a dilution curve based at least in part on at least one of the first response and the second response; and
   determine the physiological parameter of the subject based at least in part on a time integral of the dilution curve.

19. The system of claim 12, wherein the physiological parameter comprises an intrathoracic blood volume, an intrathoracic circulatory volume, a global end-diastolic volume, a pulmonary circulatory volume, or any combination thereof.

20. The system of claim 12, wherein the physiological parameter comprises a pulse rate, a blood pressure, an arterial blood oxygen saturation, a venous blood oxygen saturation, an oxygenated hemoglobin concentration, a deoxygenated hemoglobin concentration, or any combination thereof.

21. The system of claim 1, wherein the physiological parameter comprises an intrathoracic blood volume, an intrathoracic circulatory volume, a global end-diastolic volume, a pulmonary circulatory volume, or any combination thereof.

* * * * *